(12) United States Patent
Ein-Eli et al.

(10) Patent No.: US 9,145,341 B2
(45) Date of Patent: Sep. 29, 2015

(54) PROCESS OF PREPARING GRIGNARD REAGENT

(71) Applicant: Technion Research & Development Foundation Limited, Haifa (IL)

(72) Inventors: Yair Ein-Eli, Haifa (IL); Daniel Luder, Haifa (IL); Alexander Kraytsberg, Yokneam (IL)

(73) Assignee: Technion Research & Development Foundation Limited, Haifa (IL)

( * ) Notice: Subject to any disclaimer, the term of this patent is extended or adjusted under 35 U.S.C. 154(b) by 14 days.

(21) Appl. No.: 14/083,842

(22) Filed: Nov. 19, 2013

(65) Prior Publication Data
US 2014/0142332 A1 May 22, 2014

Related U.S. Application Data

(60) Provisional application No. 61/728,037, filed on Nov. 19, 2012.

(51) Int. Cl.
| | |
|---|---|
| *C25B 3/12* | (2006.01) |
| *C07B 49/00* | (2006.01) |
| *C25B 15/08* | (2006.01) |
| *H01M 4/38* | (2006.01) |
| *H01M 12/06* | (2006.01) |

(52) U.S. Cl.
CPC . *C07B 49/00* (2013.01); *C25B 3/12* (2013.01); *C25B 15/08* (2013.01); *H01M 4/382* (2013.01); *H01M 12/06* (2013.01); *H01M 2300/0045* (2013.01)

(58) Field of Classification Search
USPC ................... 205/413, 404, 395, 355
See application file for complete search history.

(56) References Cited

U.S. PATENT DOCUMENTS 3,118,825 A * 1/1964 Linsk ........................... 205/458

OTHER PUBLICATIONS

Handy "Grignard Reactions in Irnidazoliurn Ionic Liquids", The Journal of Organic Chemistry, 71(12): 4659-4662, Jun. 9, 2006.
Law et al., "Grignard Reagents in Ionic Liquids", Chemical Communications, 23: 2457-2459, Jun. 21, 2006.
Lu et al., "On the Electrochemical Behavior of Magnesium Electrodes in Polar Aprotic Electrolyte Solutions", Journal of Electroanalytical Chemistry, 466(2): 203- 217, 1999.
Luder et al., "Catalyst-Free Electrochemical Grignard Reagent Synthesis With Room-Temperature Ionic Liquids", ChemElectroChem, p. 1-4, Published Online on Jul. 15, 2013.
Meitav et al., "Solid Electrolyte Interphase (SEI) Electrode. II. The Formation and Properties of the SEI on Magnesium in $SOCl_2$-$Mg(AlCl_4)_2$ Solutions", Journal of the Elctrochemical Society, 128(4): 825-831, 1981.
Yoshimoto et al., "Mixed Electrolyte Consisting of Ethylmagnesiumbromide With Ionic Liquid for Rechargeable Magnesium Electrode", Journal of Power Sources, 195(7): 2096-2098, 2010.

* cited by examiner

*Primary Examiner* — Sudhakar Katakam
*Assistant Examiner* — Pancham Bakshi

(57) ABSTRACT

A novel process of preparing a Grignard reagent is disclosed. The process is effected by electrochemically reacting a Grignard precursor with an electrode which comprises a metal for forming the Grignard reagent, in the presence an electrolyte solution that comprises a room temperature ionic liquid (RTIL). Electrochemical cells and systems for performing the process, and uses thereof in various applications are also disclosed.

19 Claims, 19 Drawing Sheets
(16 of 19 Drawing Sheet(s) Filed in Color)

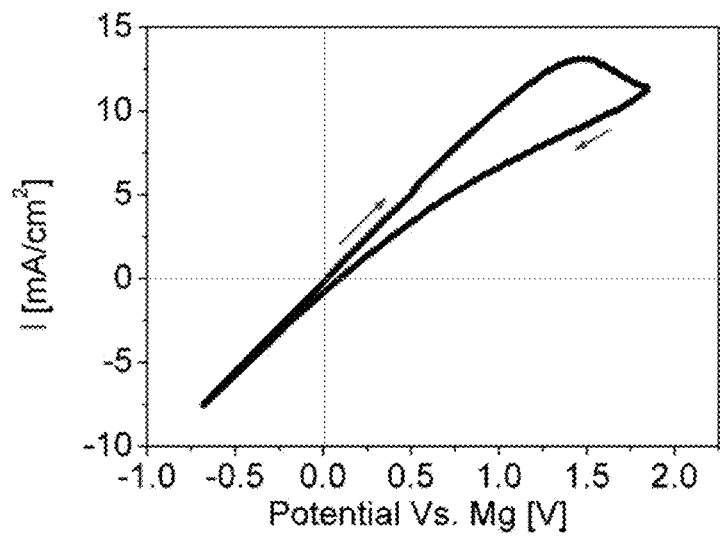
FIG. 13
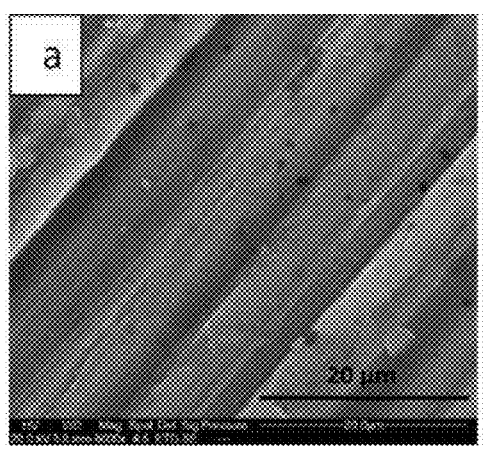 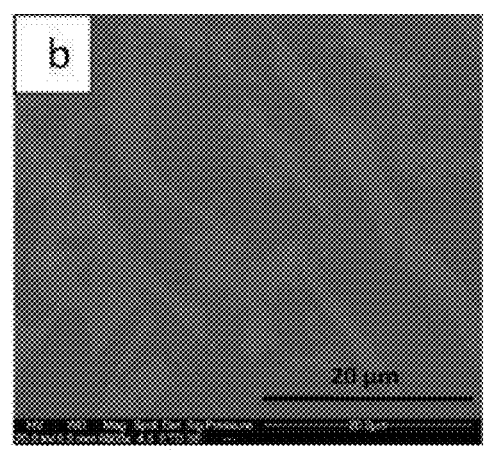
FIG. 14A             FIG. 14B

PROCESS OF PREPARING GRIGNARD REAGENT

RELATED APPLICATION

This application claims the benefit of priority under 35 USC §119(e) of U.S. Provisional Patent Application No. 61/728,037 filed Nov. 19, 2012, the contents of which are incorporated herein by reference in their entirety.

FIELD AND BACKGROUND OF THE INVENTION

The present invention, in some embodiments thereof, relates to chemical synthesis and, more particularly, but not exclusively, to a novel process of preparing Grignard reagents and to uses thereof in organic syntheses.

Metal-organic compounds are widely used in the industry to produce fine chemicals as well as pharmaceutical agents with complex molecule structures. The most common type of such metal-organic compounds is the Grignard reagent (herein also referred to interchangeably as GR), which is formed by the reaction of an organic halide with Magnesium or a similar metal.

Grignard reagent is used in numerous industrial processes involving reactions with C—C bond formation. Examples of industrial processes which utilize Grignard reagent include the synthesis of tramadol [Kleemann et al. Pharmaceutical Substances; Thieme-Verlag: Stuttgart (Germany), 2000; pp. 2085.]; syntheses of various organo-tin compounds [Stoermer, M. J.; Pinhey, J. T. Molecules 1998, 3, M67] used as stabilizers for vinyl chloride resins, catalysts for hardening urethane and other industrial purposes; production of organo-silicon products [Narain, R. P. Mechanisms in organic chemistry; New age international: New Delhi, 2008]; production of organo-phosphorous compounds used for vitamin synthesis [Kolodiazhnyi, O. I. Phosphorous Ylides, chemistry and application in organic synthesis; Wiley-VCH: New-York, 1999] and production of organo-boron compounds used for conjugated polymer synthesis [Tanaka, K.; Chujo, Y. Macromolecular Rapid Communications 2012, 15, 1235-1255]; production of tamoxifen derivatives used in the pharmaceutical industry of flavor enhancers for the food industry in the form of maltol or ethyl maltol, of various anti-inflammatory analgesics such as Naproxen, of pharmaceuticals for pain treatment such as propoxyphene [Richey, H. Grignard reagents—new developments; John Wiley and sons, LTD: New York, 2000] and many other uses.

Grignard reagents form via the reaction of an alkyl or aryl halide with magnesium metal. The reaction proceeds through single electron transfer, as depicted in Scheme 1 below:

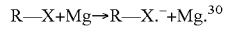

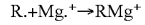

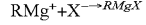

Scheme 1 wherein R is alkyl, cycloalkyl or aryl and X is halide.

Alkyl and aryl bromides and iodides are common substrates for preparing Grignard reagent. Chlorides are also used, and fluorides are generally unreactive, except with specially activated magnesium. The reactions involved in preparing a Grignard reagent are typically highly exothermic.

The solvent media plays a key role in formation of Grignard reagent and its following reactions. The most suitable and universally used solvents are ethers, specifically tetrahydrofuran (THF) or diethyl ether.

In practice, the production of Grignard reagent is often difficult, as the surface of the magnesium is usually covered by a layer of hydroxides and oxides such as MgO, which impairs the reaction of the Mg-metal with organic halides. In particular, when Mg is in contact with different organic media, a non-conductive passivation layer is present and slows down or completely prevents chemical and electrochemical reactions that would otherwise occur in its absence [Lu et al. J Electroanal Chem 1999, 2, 203-217; Meitav, A.; Peled, E. J. Electrochem. Soc. 1981, 4, 825-831].

Different initiating methods have been introduced to the synthesis procedure in order to weaken the passivating layer of MgO, and thereby exposing highly reactive magnesium to the organic halide. Mechanical methods include crushing of the Mg pieces in situ, rapid stirring, and sonication of the suspension. Chemical methods involve activating agents such as iodine, methyl iodide, and 1,2-dibromoethane. Physical methods include application of heat and environmental dryness.

Grignard reagents are produced in industry for use in situ, or for sale. As with at bench-scale, the main problem is that of initiation; a portion of a previous batch of Grignard reagent is often used as the initiator.

Grignard reactions are exothermic, and this exothermicity must be considered when a reaction is scaled-up from laboratory to production plant.

Grignard reagents such as methylmagnesium bromide, methylmagnesium chloride, phenylmagnesium bromide, and allylmagnesium bromide are available commercially as tetrahydrofuran or diethyl ether solutions.

Efforts to synthesize GR electrochemically in ethers have been characterized as hazardous and resulted in low yields per unit time [Richey, H. (2000) supra].

Other efforts, which attempt regular chemical GR synthesis in a separate step, suffer from numerous problems such as reduced safety, non-controllability and sluggish reaction rates. In addition, carrying out GR synthesis in a separate step rather than integrating it into a single process combined with subsequent reaction steps, leads to higher costs.

Room temperature ionic liquids, abbreviated RTILs, are a relatively new class of solvents that have been studies thoroughly for the past two decades as an electrolyte media. RTILs are liquids at room temperature that are composed essentially of 100% ions excluding contaminations. Typically, in RTIL, the cations are organic and anions are inorganic.

RTILs are characterized by a wide electrochemical window, low volatility and vapor pressure, high conductivity, chemical stability, low boiling temperature, environmental friendliness and having the ability to adjust different properties by minutely adding or subtracting functional groups on the cation.

Because of these properties, RTILs have found many applications in diverse areas such as bioscience, $CO_2$ capture, organic synthesis and energy management. In particular, a large number of uses have been found in electrochemistry for applications such as electrodeposition, batteries, fuel cells, solar cells, and capacitors.

In the area of Mg electrochemistry, certain non-acidic ionic liquids such as [1-butyl-1-methyl pyrolidinium bis(trifluoromethylsulfonyl)imide] (BMPTFSI) and [N,N-diethyl-N-methyl-N-(2-methoxyethyl) ammonium-bis(trifluoromethylsulfonyl) imide] (DEMETFSI) have been found to be suitable as co-solvents for externally added GRs such as phenyl-magnesium bromide (PhMgBr) and ethyl-magnesium bromide (EtMgBr) [Lu et al., 1999, supra; and Yoshimoto et al. Power Sources 2010, 7, 2096-2098].

Additional background art includes Handy S. T., *J. Org. Chem.*, 2006, 71 (12), pp. 4659-4662, which teaches non-electrochemical Grignard reactions utilizing RTIL as a solvent; and Law et al., *Chem. Commun.*, 2006, pp. 2457-2459.

SUMMARY OF THE INVENTION

According to an aspect of some embodiments of the present invention there is provided a process of preparing a Grignard Reagent of a formula RMX, the process comprising: electrochemically reacting an electrode comprising the M metal with a Grignard precursor having a formula RX in the presence of a non-aqueous electrolyte solution comprising a room temperature ionic liquid (RTIL), wherein:

R is selected from the group consisting of alkyl, alkenyl, alkynyl, cycloalkyl, aryl, heteroaryl, heteroalicyclic, alkoxy, aryloxy, thioalkoxy, thioaryloxy, carboxy, thiocarboxy, carbamate, thiocarbamate, amide, thioamide, carbonyl, thiocarbonyl, urea, and thiourea; M is a metal suitable for forming a Grignard reagent; and X is halide, thereby preparing the Grignard Reagent.

According to some embodiments of the present invention, the metal M is selected from the group consisting of magnesium and lithium.

According to some embodiments of the present invention, the room temperature ionic liquid comprises a cation selected from the group consisting of a substituted or unsubstituted imidazolium, a substituted or unsubstituted morpholinium, a substituted or unsubstituted oxazolium, a substituted or unsubstituted piperidinium, a substituted or unsubstituted pyrazinium, a substituted or unsubstituted pyrazolinium, a substituted or unsubstituted pyrazolium, a substituted or unsubstituted pyridazinium, a substituted or unsubstituted pyridinium, a substituted or unsubstituted pyrimidinium, a substituted or unsubstituted pyrrolidinium, a substituted or unsubstituted thiazolium, a substituted or unsubstituted triazolium, a substituted or unsubstituted 1,2,4-triazolinium, a substituted or unsubstituted 1,2,3,4-tetrazolinium, phosphonium, sulfonium, uronium, guanidinium, 3-alkyl-1-methylimidazolium, 1-alkylpyridinium, N-methyl-N-alkylpyrrolidinium, 1-methyl-4-alkyl-1,2-triazolinium, 1-methyl-(2, 3 or 4)-alkyltetrazolinium and tetraalkylammonium.

According to some embodiments of the present invention, an anion of the room temperature ionic liquid is selected from the group consisting of a halide, a triflate and bis(trifluoromethylsulfonyl)imide.

According to some embodiments of the present invention, the room temperature ionic liquid is [1-butyl 1-methyl pyrolidinium bis(trifluoromethylsulfonyl)imide].

According to some embodiments of the present invention, the non-aqueous solution further comprises a polar non-aqueous solvent.

According to some embodiments of the present invention, the solvent comprises ether.

According to some embodiments of the present invention, the ether is selected from the group consisting of diethyl ether, THF and ether having a boiling point higher than 80° C.

According to some embodiments of the present invention, a concentration of the room temperature ionic liquid is the non-aqueous solution is at least 5 volume percents.

According to some embodiments of the present invention, the electrolyte solution comprises the room temperature ionic liquid and a non-aqueous polar solvent at a volumetric ratio that ranges from 10:1 to 1:10.

According to some embodiments of the present invention, the ratio is 1:1.

According to some embodiments of the present invention, a concentration of the Grignard precursor in the electrolyte solution ranges from 1 to 50 volume percents.

According to some embodiments of the present invention, a sum of a concentration of the Grignard precursor and a concentration of the room temperature ionic liquid is at least 10 volume percents of the electrolyte solution.

According to some embodiments of the present invention, the electrochemically reacting comprises electrically connecting the electrode comprising the M metal with a counter electrode, wherein each of the electrode comprising the M metal and the counter electrode contacts the electrolyte solution.

According to some embodiments of the present invention, the electrochemically reacting further comprises generating an electric current between the electrodes.

According to some embodiments of the present invention, generating the electric current comprises generating a current density that ranges from 1 to 5 mA/cm$^2$.

According to some embodiments of the present invention, the electrode containing the M metal functions as an anode during the electrochemically reacting.

According to some embodiments of the present invention, the Grignard reagent and/or an amount of the Grignard reagent obtained by the process is identifyable by an analytical method selected from the group consisting of a color reaction and NMR.

According to some embodiments of the present invention, the process further comprises isolating the Grignard reagent.

According to an aspect of some embodiments of the present invention there is provided an electrochemical cell comprising a working electrode and a counter electrode being electrically connected to one another, the working electrode comprising a metal M, the metal M being suitable for forming a Grignard reagent, the electrochemical cell being operable by introducing thereto a Grignard precursor having Formula RX and a non-aqueous electrolyte solution comprising a room temperature ionic liquid (RTIL), wherein: R is selected from the group consisting of alkyl, alkenyl, alkynyl, cycloalkyl, aryl, heteroaryl, heteroalicyclic, alkoxy, aryloxy, thioalkoxy, thioaryloxy, carboxy, thiocarboxy, carbamate, thiocarbamate, amide, thioamide, carbonyl, thiocarbonyl, urea, and thiourea; M is a metal suitable for forming a Grignard reagent; and X is halide.

According to some embodiments of the present invention, the metal M is selected from the group consisting of magnesium and lithium.

According to some embodiments of the present invention, the non-aqueous electrolyte solution further comprises a polar non-aqueous solvent.

According to some embodiments of the present invention, the solvent comprises ether, as described herein.

According to some embodiments of the present invention, the counter electrode is selected from the group consisting of a Mg-containing electrode and a Pt-containing electrode.

According to some embodiments of the present invention, the electrode comprising the metal M functions as an anode in the cell.

According to some embodiments of the present invention, the cell further comprises a voltage source electrically connected to the counter electrode and the working electrode.

According to some embodiments of the present invention, the cell further comprises the non-aqueous electrolyte solution such that the working electrode and the counter electrode are being in contact with the electrolyte solution.

According to some embodiments of the present invention, the cell further comprises the Grignard precursor.

According to some embodiments of the present invention, the electrochemical cell is operable by generating a current between the working electrode and the counter electrode.

According to some embodiments of the present invention, the electrochemical is operable as a battery.

According to some embodiments of the present invention, in the battery, the counter electrode is a cathode configured as an air cathode.

According to an aspect of some embodiments of the present invention there is provided a method of preparing a compound synthesizable by a synthesis that comprises a Grignard-type reaction, the method comprising: preparing a Grignard reagent having a formula RMX by electrochemically reacting a Grignard precursor of a formula RX with an electrode which comprises metal M, in the presence of an electrolyte solution that comprises a room temperature ionic liquid; and performing the Grignard-type reaction with the Grignard Reagent, wherein: R is selected from the group consisting of alkyl, alkenyl, alkynyl, cycloalkyl, aryl, heteroaryl, heteroalicyclic, alkoxy, aryloxy, thioalkoxy, thioaryloxy, carboxy, thiocarboxy, carbamate, thiocarbamate, amide, thioamide, carbonyl, thiocarbonyl, urea, and thiourea; M is a metal suitable for forming a Grignard reagent; and X is halide, thereby preparing the compound.

According to some embodiments of the present invention, preparing the Grignard reagent and performing the Grignard-type reaction are effected within the same reactor.

According to an aspect of some embodiments of the present invention there is provided a compound synthesizable by a synthesis that comprises a Grignard-type reaction, prepared by a method as described herein.

According to an aspect of some embodiments of the present invention there is provided a system for preparing a compound synthesizable by a synthesis that comprises a Grignard-type reaction, the system comprising a reactor which comprises: a working electrode and a counter electrode having a liquid passage therebetween, the working electrode having a metal M, suitable for forming a Grignard reagent of a formula RMX; a first inlet port for introducing into the reactor a room temperature ionic liquid (RTIL) or an electrolyte solution comprising the RTIL, to generate a flow within the liquid passage; a second inlet port for introducing into the reactor a Grignard precursor of a formula RX, the second inlet port being positioned upstream the liquid passage, wherein: R is selected from the group consisting of alkyl, alkenyl, alkynyl, cycloalkyl, aryl, heteroaryl, heteroalicyclic, alkoxy, aryloxy, thioalkoxy, thioaryloxy, carboxy, thiocarboxy, carbamate, thiocarbamate, amide, thioamide, carbonyl, thiocarbonyl, urea, and thiourea; M is a metal suitable for forming a Grignard reagent; and X is halide.

According to some embodiments of the present invention, the reactor further comprises a third inlet port for introducing into the reactor a Grignard substrate for undergoing the Grignard-type reaction to provide a Grignard product, the third inlet port being positioned downstream the liquid passage.

According to some embodiments of the present invention, the reactor further comprises an outlet port positioned to remove the Grignard product.

According to an aspect of some embodiments of the present invention there is provided a method of polishing a metal M-containing surface of a substance, the method comprising electrochemically reacting the M-containing surface in the presence of an electrolyte solution that comprises RTIL.

According to some embodiments of the present invention, the electrolyte solution further comprises a compound of a formula RX, wherein: R is selected from the group consisting of alkyl, alkenyl, alkynyl, cycloalkyl, aryl, heteroaryl, heteroalicyclic, alkoxy, aryloxy, thioalkoxy, thioaryloxy, carboxy, thiocarboxy, carbamate, thiocarbamate, amide, thioamide, carbonyl, thiocarbonyl, urea, and thiourea; M is a metal suitable for forming a Grignard reagent; and X is halide.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
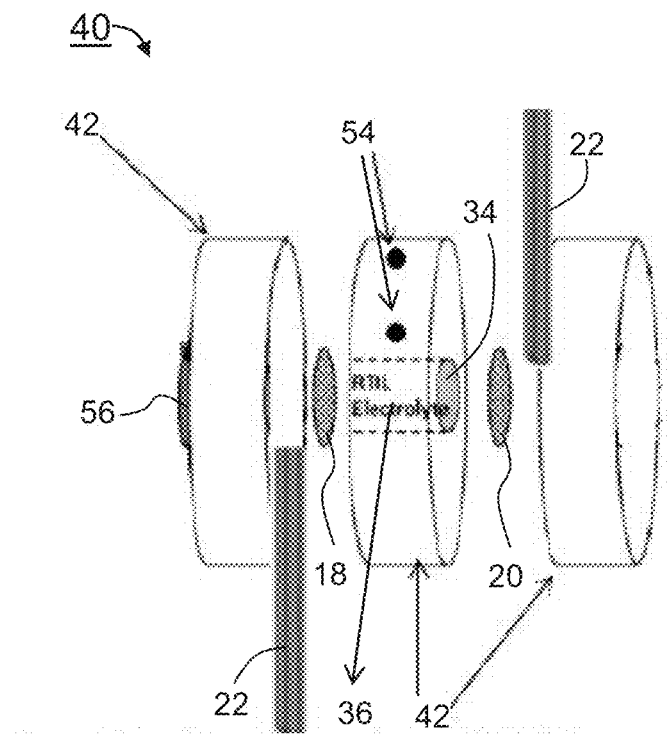
Figure 1B:
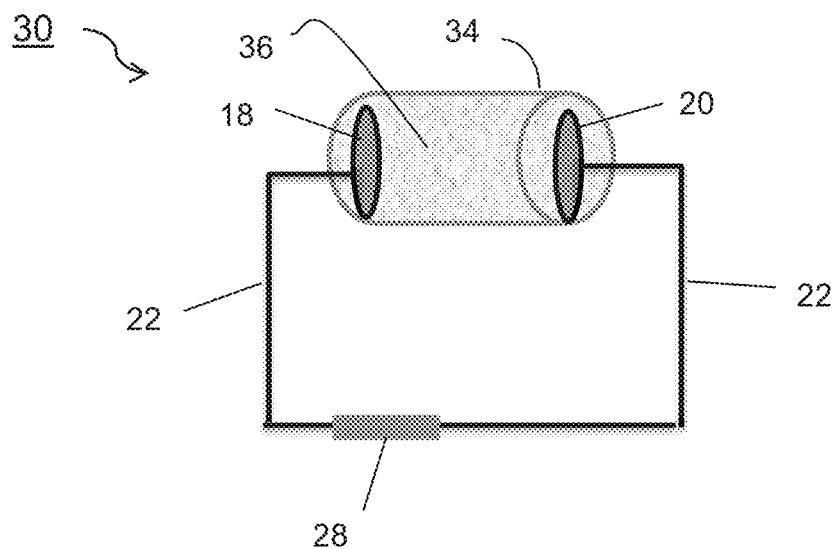

FIGS. 1A-B present schematic illustrations of exemplary electrochemical cells for carrying out a (e.g., potentiostatic) process of preparing a Grignard Reagent (GR), according to some embodiments of the present invention.

Figure 2A:
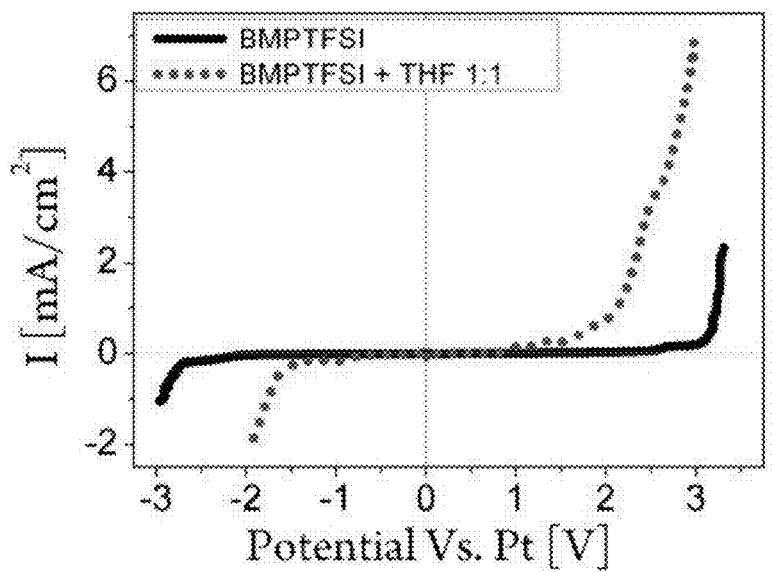
Figure 2B:
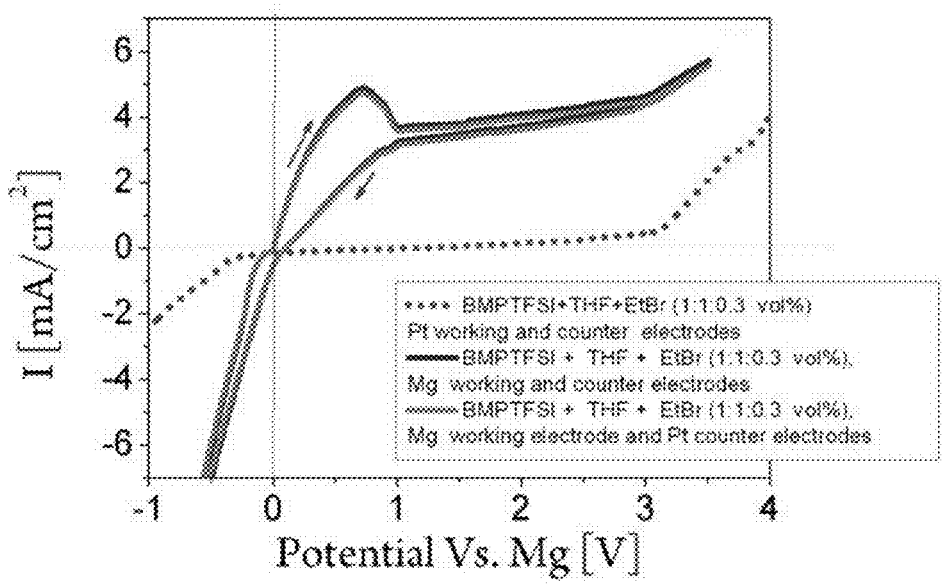
Figure 2C:
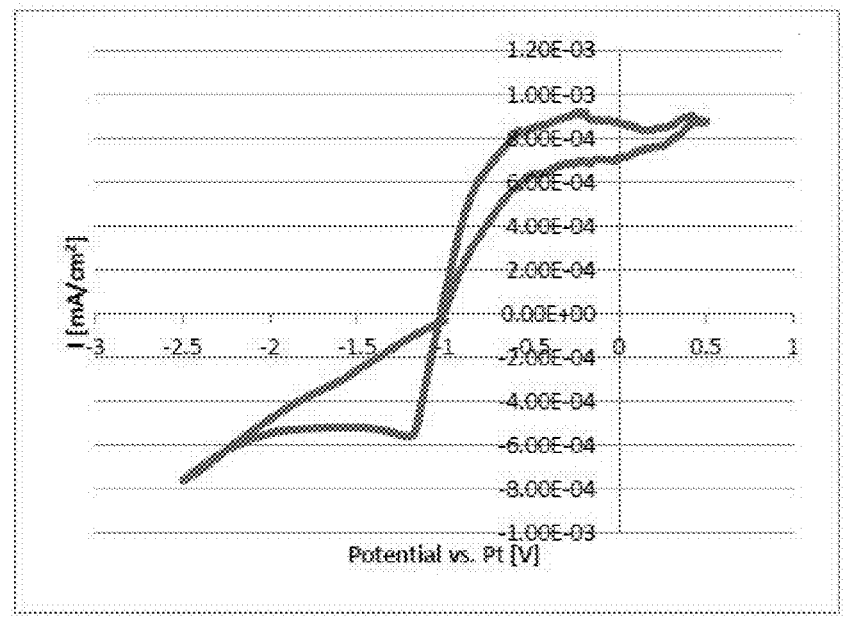
Figure 2D:
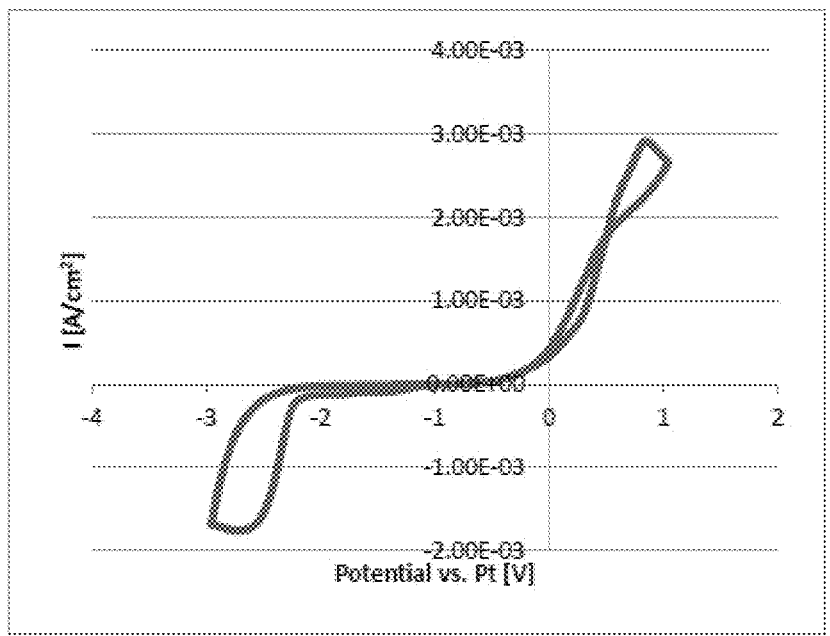

FIGS. 2A-D present cyclic voltamograms of various electrochemical cells according to some embodiments of the present invention, employing an electrolyte solution containing BMPTFSI (black) and BMPTFSI+THF (green), for reference (FIG. 2A); an electrolyte solution containing BMPTFSI+THF+EtBr (1:1:0.3 vol %) with Pt working and counter electrodes (green), with Mg working and counter electrodes (blue), and with Mg working electrode and Pt counter electrode (grey), and with Mg reference electrode (FIG. 2B); an electrolyte solution containing BMPTFSI+THF+PrBr (1:1:0.3 vol %) (FIG. 2C); and an electrolyte solution containing BMPTFSI+THF+PhBr (1:1:0.3 vol %) (FIG. 2D).

Figure 3:
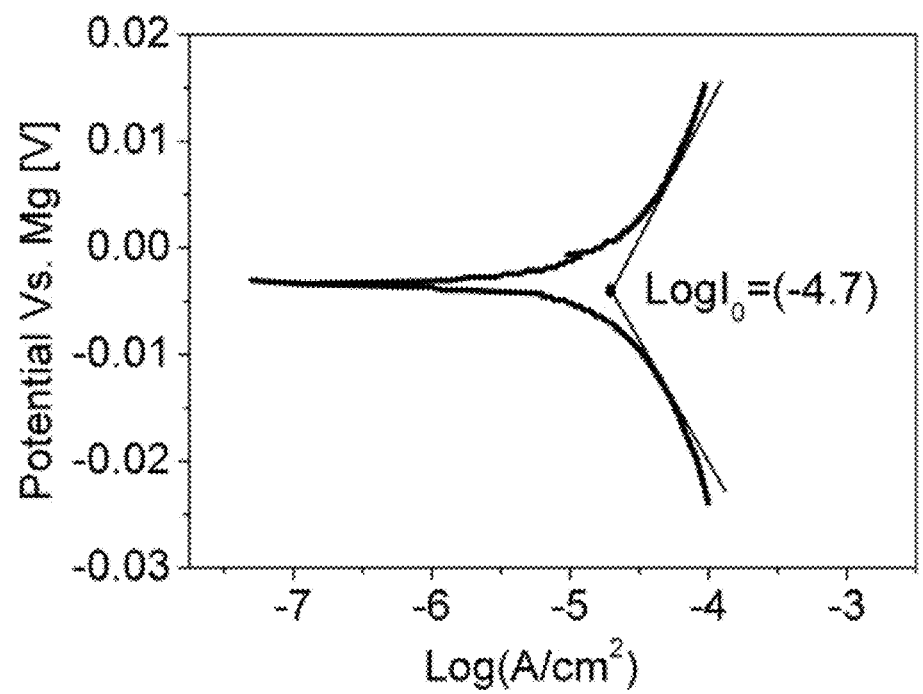

FIG. 3 presents an Evans diagram presenting anodic and cathodic linear polarization of Mg working electrode in BMPTFSI+THF+EtBr (1:1:0.3 vol %) electrolyte solution vs. Mg counter electrode). Scan rate: 5 mV/sec.

Figure 4:
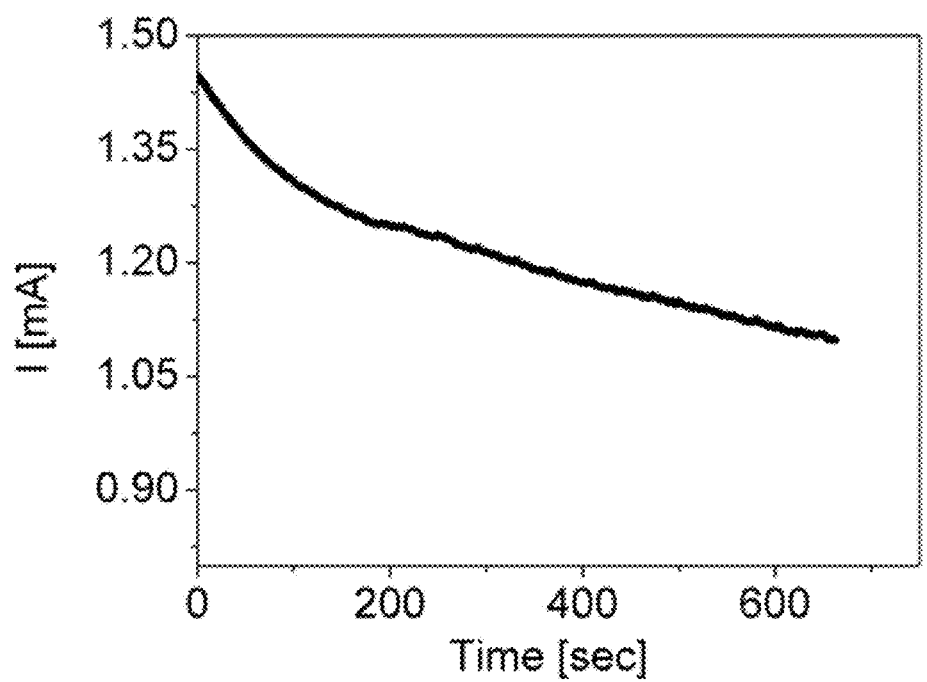

FIG. 4 presents a potentiostatic curve recorded at 0.2 [V] vs. Mg for an electrochemical cell having Mg working and counter electrodes and an electrolyte solution containing BMPTFSI+THF+EtBr (1:1:0.3 vol %).

Figure 5A:
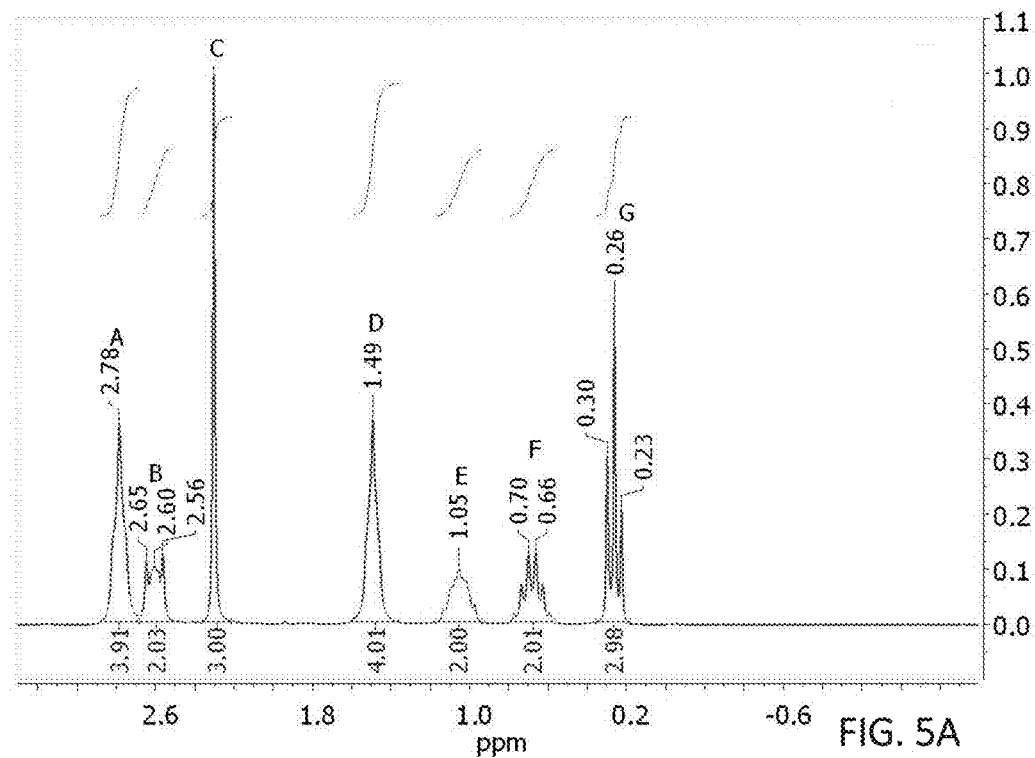
Figure 5B:
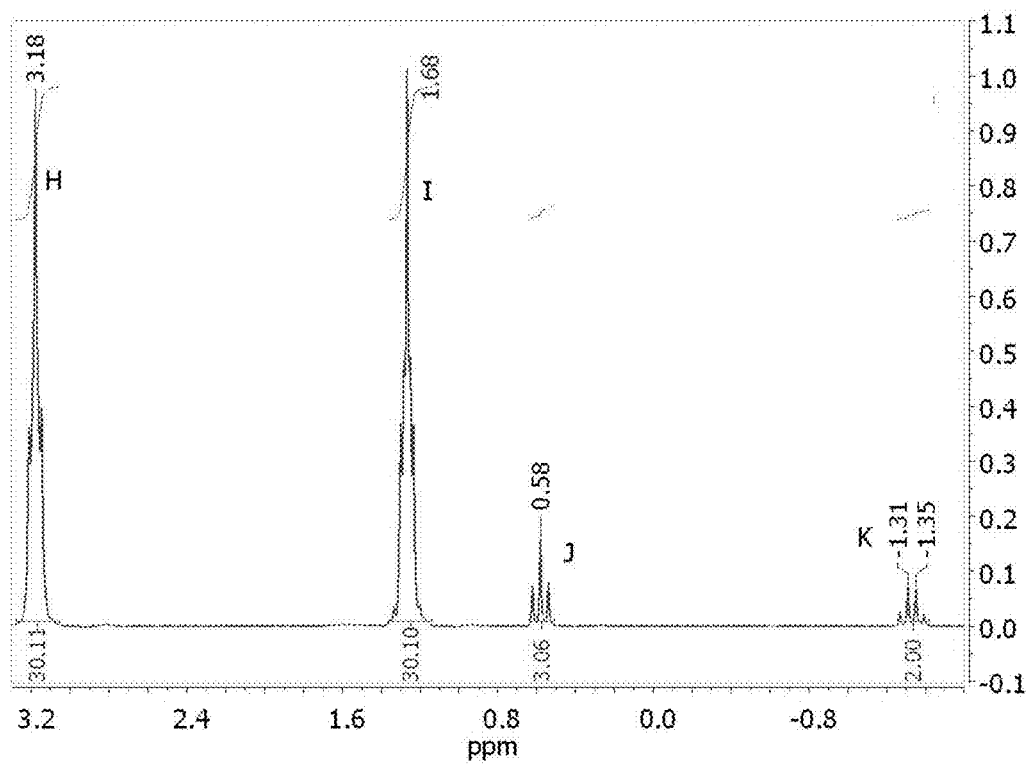
Figure 5C:
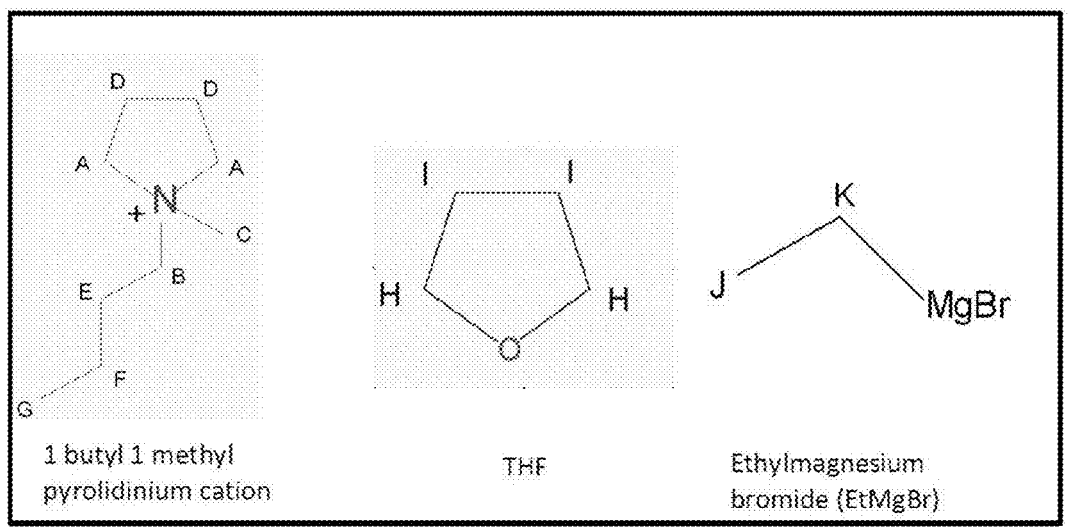

FIGS. 5A-C present $^1$H-NMR spectra of pure BMPTFSI cation (1-butyl 1-methyl pyrolidinium (FIG. 5A), and of EtMgBr in THF, 1.2M (FIG. 5B), and the structure and signal ascription of BMPTFSI cation, THF and EtMgBr (FIG. 5C).

Figure 6:
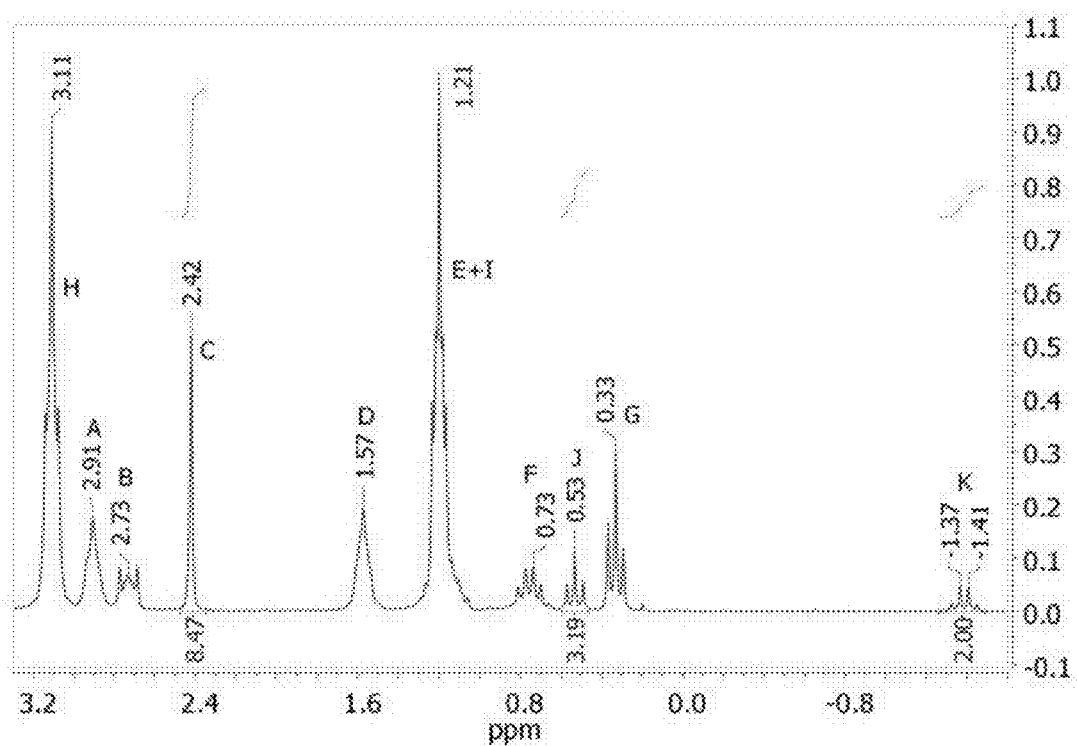

FIG. 6 presents a $^1$H-NMR spectrum of a reference solution prepared by mixing BMPTFSI and THF/EtMgBr (1.2M) at a 1:1 vol ratio.

Figure 7A:
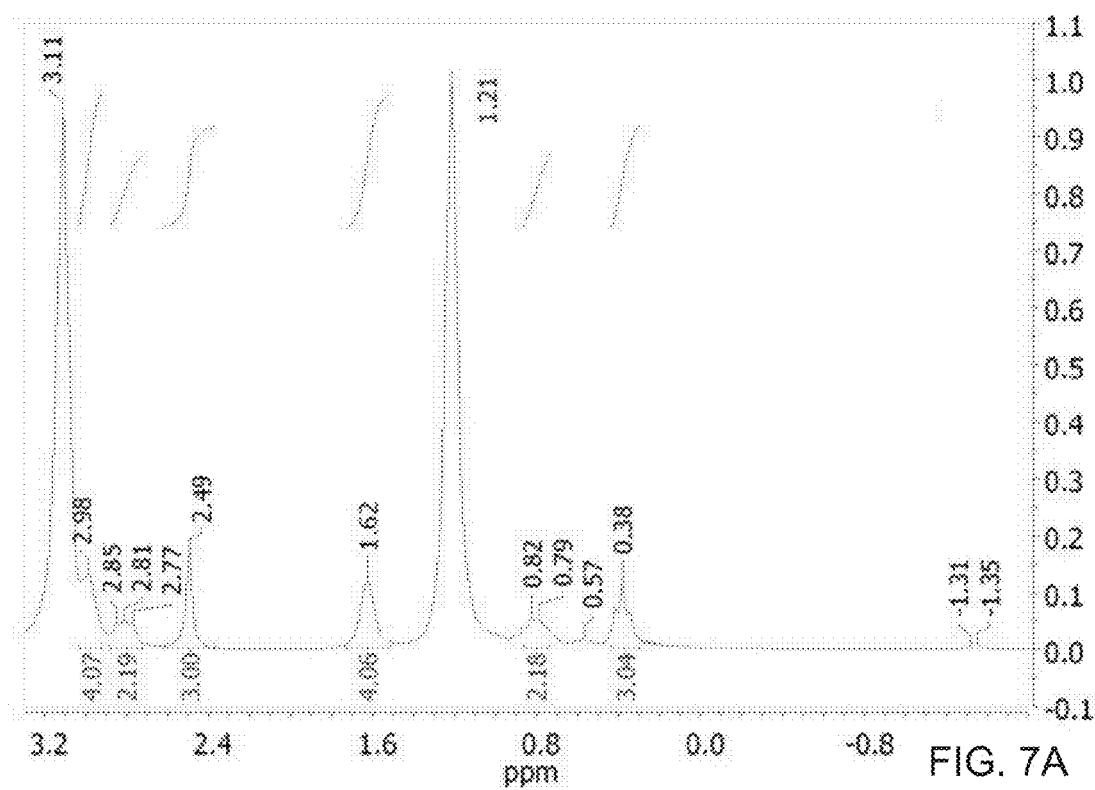
Figure 7B:
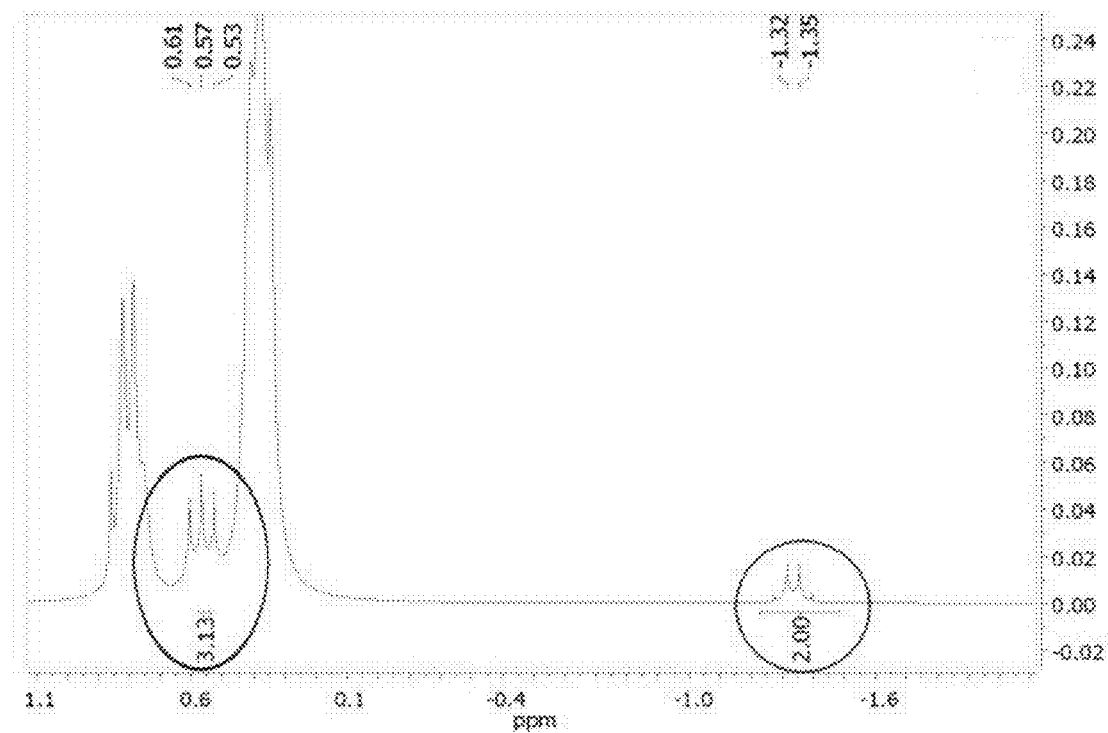
Figure 7C:
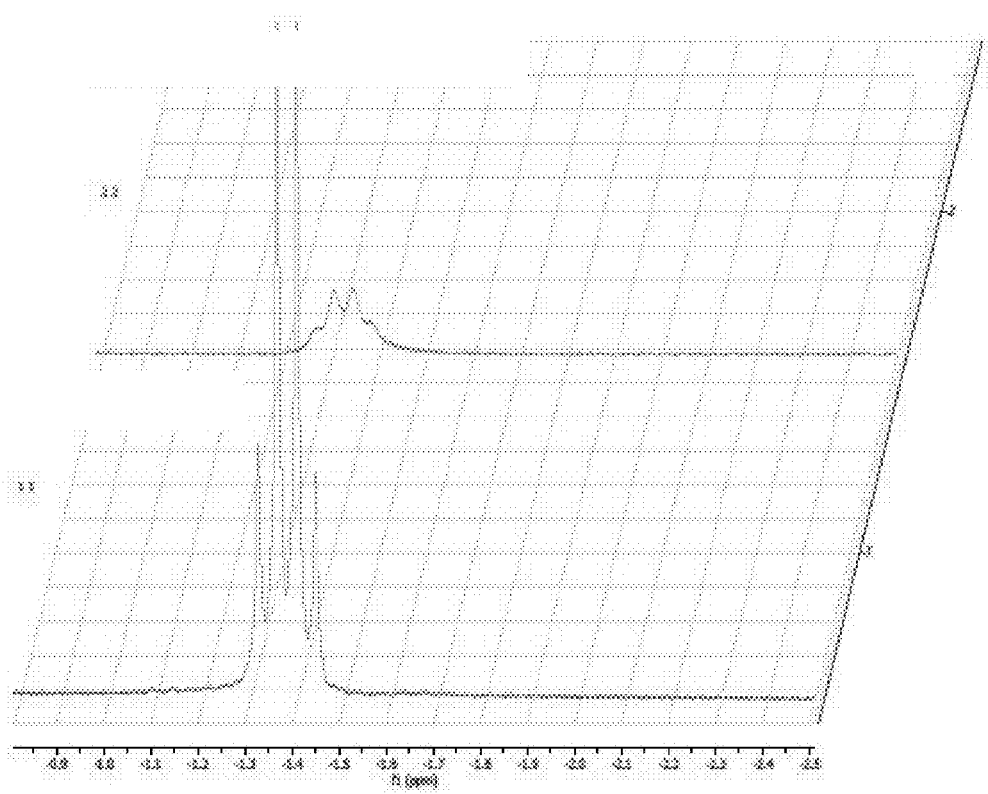

FIGS. 7A-C present A $^1$H-NMR spectrum of a reaction solution obtained in a potentiostatic process according to some embodiments of the present invention, using an electrolyte solution containing BMPTFSI+THF+EtBr (1:1:0.3 vol %), in which the total charge transfer was 0.805 [C], an expansion (showing the 0.9-(-1.6) ppm range) of the $^1$H-NMR spectrum presented in FIG. 7A (FIG. 7B); and an expansion of $^1$H-NMR spectra exhibited in FIG. 7A (top) and FIG. 6 (bottom) around the signal ascribed to the H atoms bonded to "K" carbon of EtMgBr shown in FIG. 5B (FIG. 7C).

Figure 8:
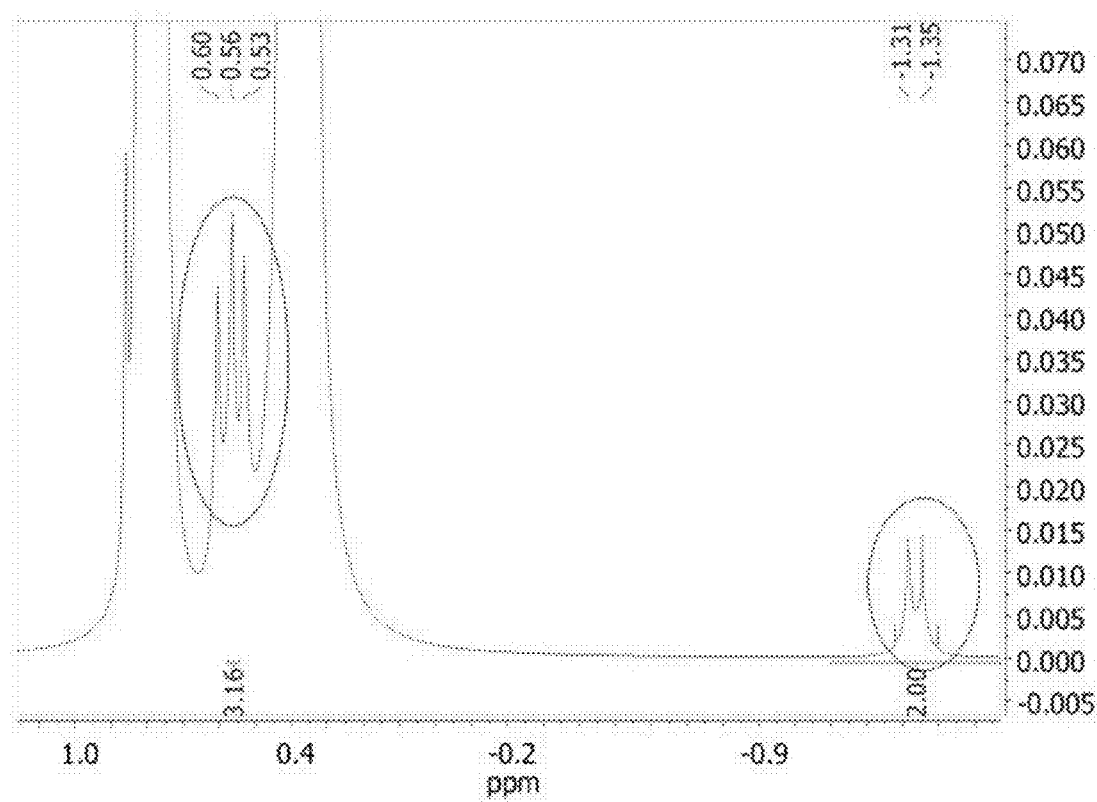

FIG. 8 presents an expansion of $^1$H-NMR spectrum of a reaction solution obtained in a potentiostatic process according to some embodiments of the present invention, using an electrolyte solution containing BMPTFSI+TEGDME+EtBr (1:1:0.3 vol %), in which the total charge transfer was 0.441 [C].

Figure 9:
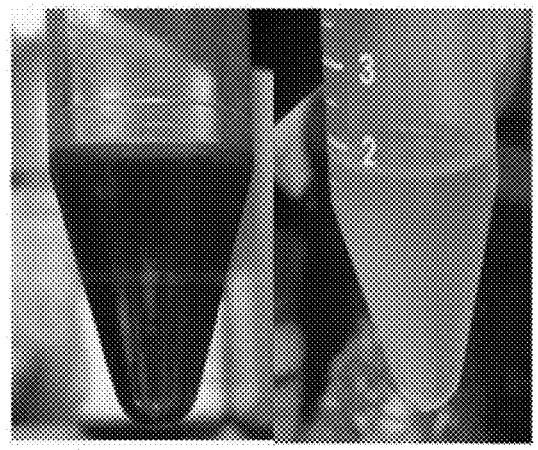

FIG. 9 presents photographs showing an exemplary solution before titration (left) and after titration (right) during measurements, via a volumetric titration method, of a concentration of EtMgBr obtained in a process according to some embodiments of the present invention.

Figure 10:
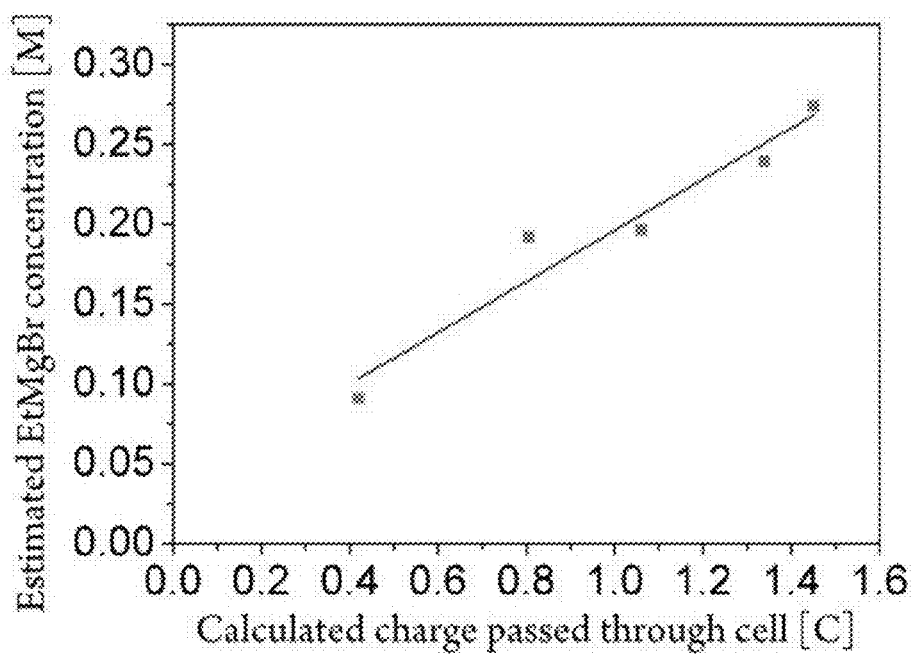

FIG. 10 presents a plot showing a concentration of the obtained EtMgBr vs. total charge passed through cell in potentiostatic processes performed according to some embodiments of the present invention.

Figure 11:
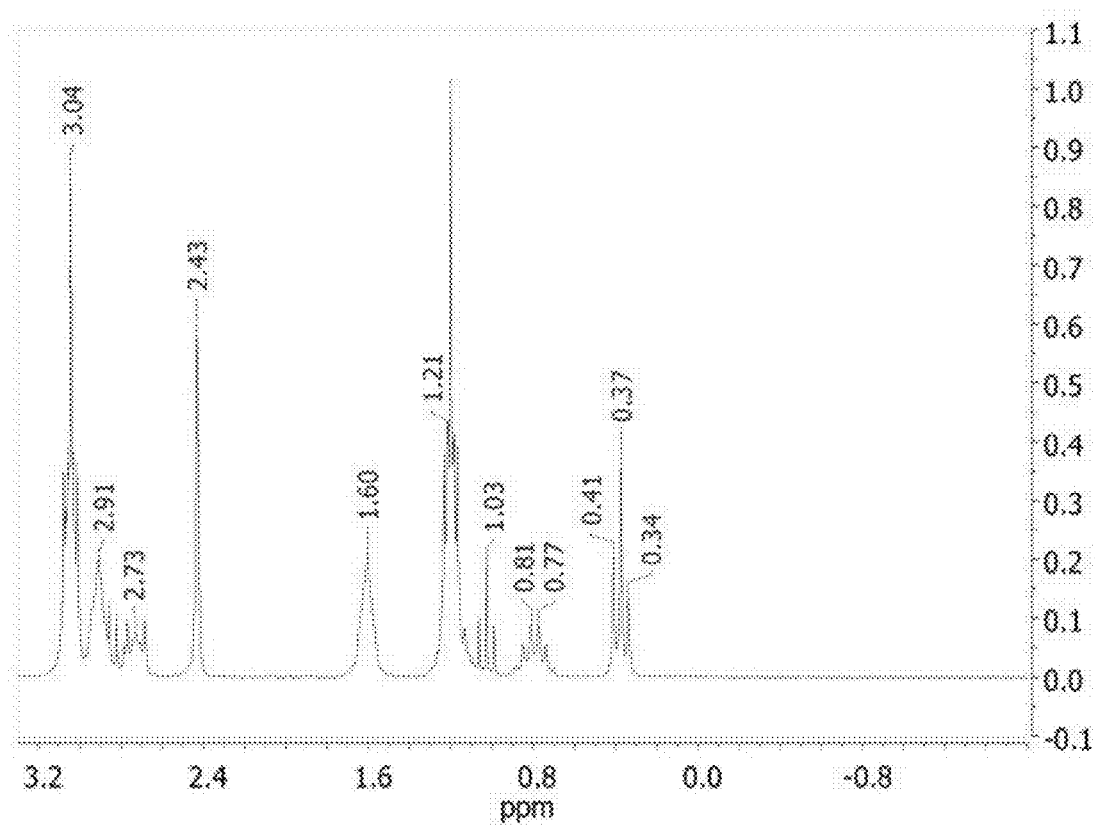

FIG. 11 presents $^1$H-NMR analysis of a solution prepared by mixing BMPTFSI, THF and EtBr (1:1:0.3 vol % ratio) after resting in cell for 1500 seconds without potential application (Cell assembled with two magnesium electrodes).

Figure 12:
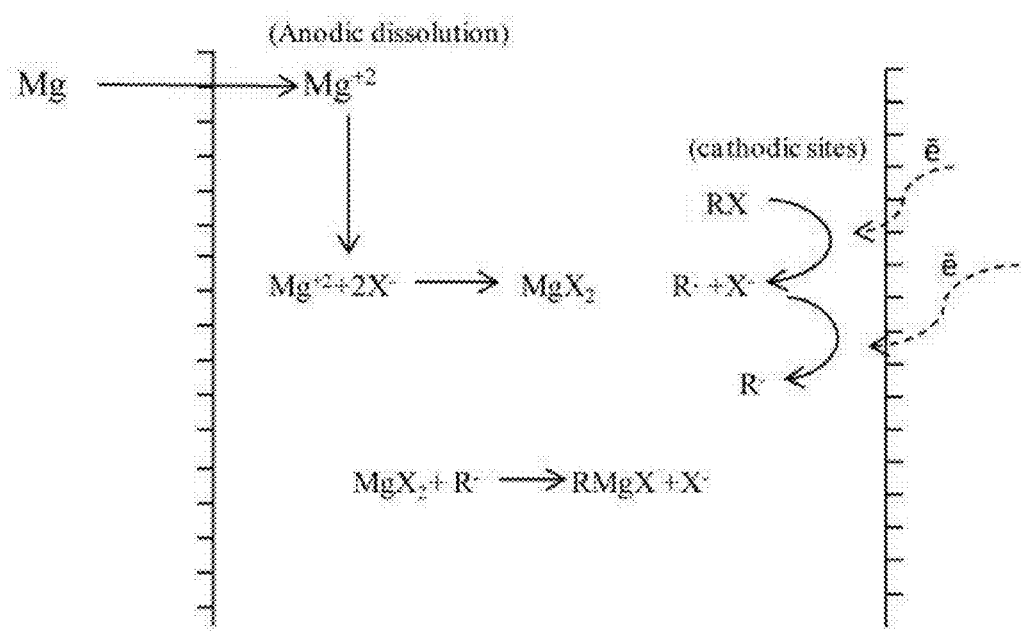

FIG. 12 presents a schematic illustration of a proposed mechanism of the preparation of an exemplary Grignard Reagent during an electrochemical process according to some embodiments of the present invention.

FIG. 13 presents a cyclic voltamogram collected at 50 mV/sec. for an electrochemical cell containing magnesium working and counter electrodes and an electrolyte solution containing BMPTFSI+THF+EtBr at 1:1:0.3 vol %.

FIGS. 14A-B present SEM images, secondary electron contrast (SE) of the Mg surface of a Mg electrode of an exemplary electrochemical cell according to some embodiments of the present invention before (FIG. 14A) and after (FIG. 14B) CV.

Figure 15:
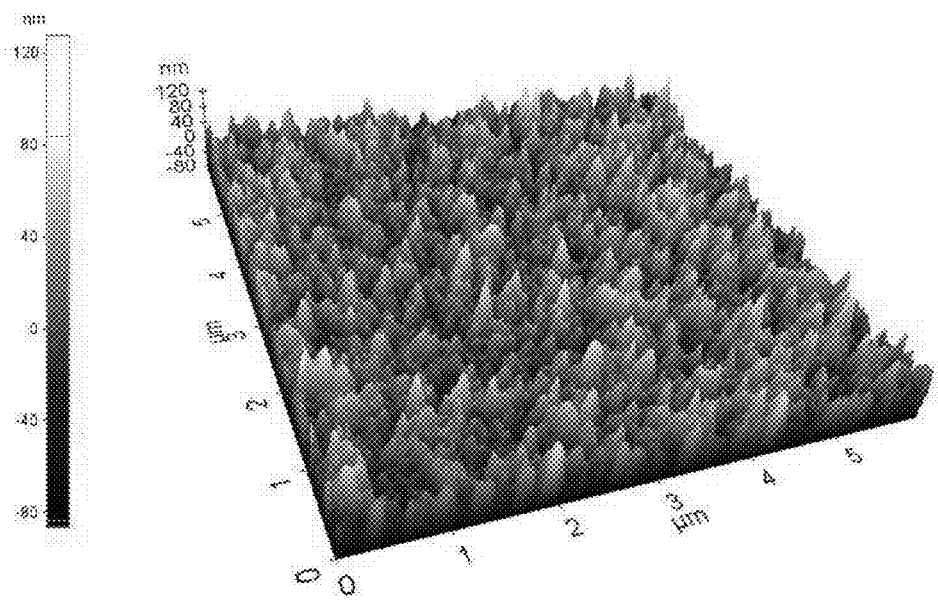

FIG. 15 presents an AFM image of the Mg electrode's surface after CV as described in FIG. 14B.

Figure 16A:
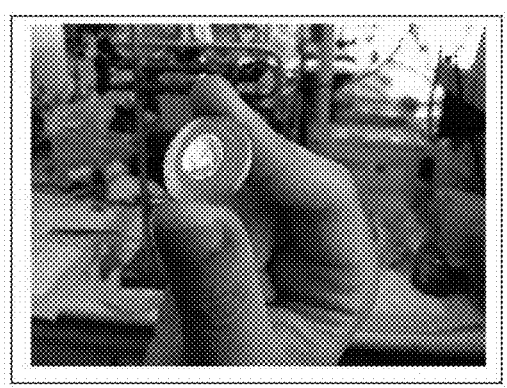
Figure 16B:
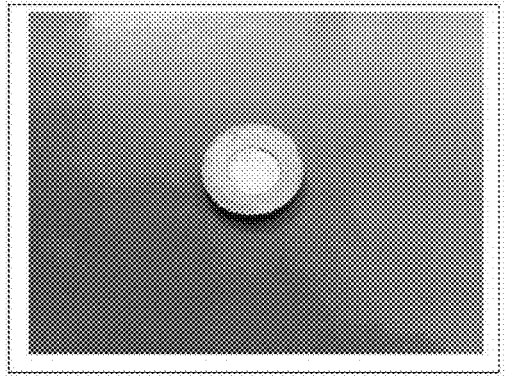

FIGS. 16A-B present photographs of the Mg electrode's surface after CV as described in FIG. 14B (FIG. 16A).

Figure 17:
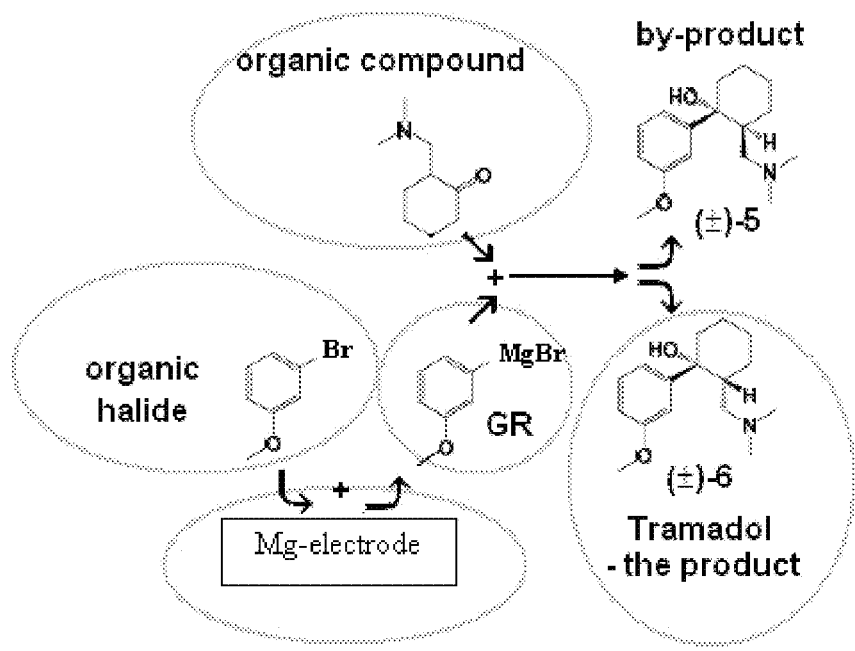

FIG. 17 presents a schematic illustration of a flow reaction of preparing Tramadol using a process of preparing GR according to some embodiments of the present invention.

Figure 18:
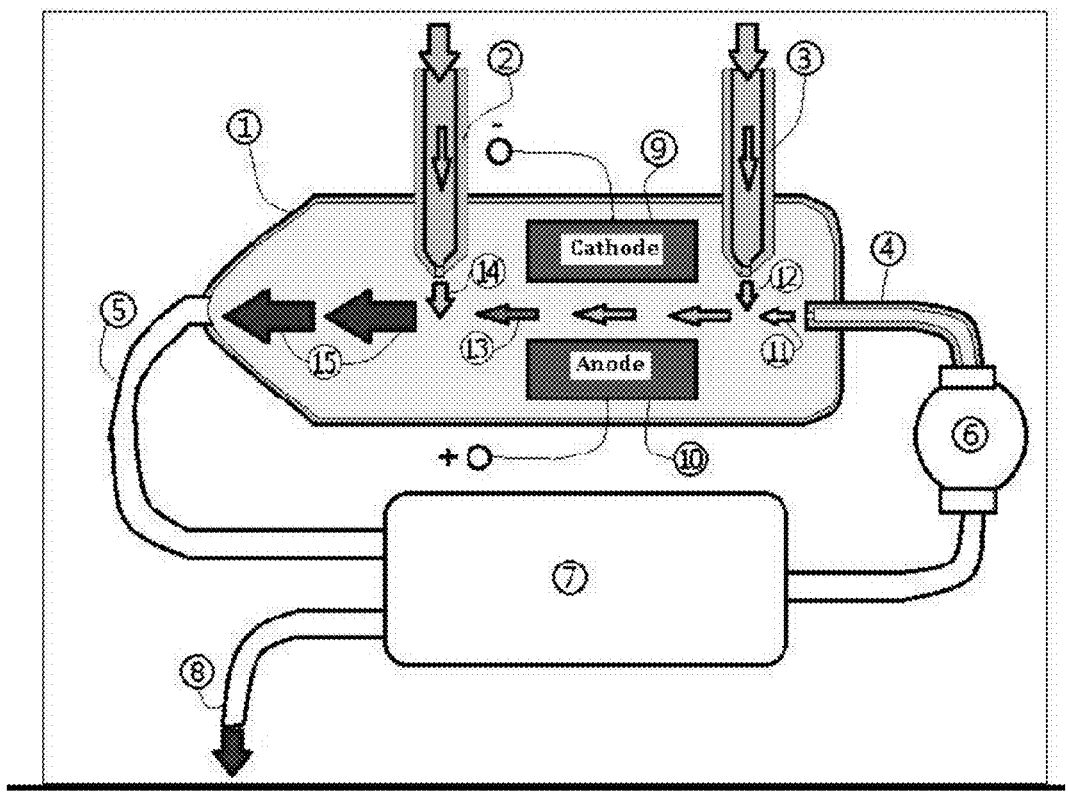

FIG. 18 is a schematic illustration of a reactor prototype for performing synthesis of an organic compound using a Grignard-type reaction and a process of preparing a Grignard Reagent according to some embodiments of the present invention.

Figure 19:
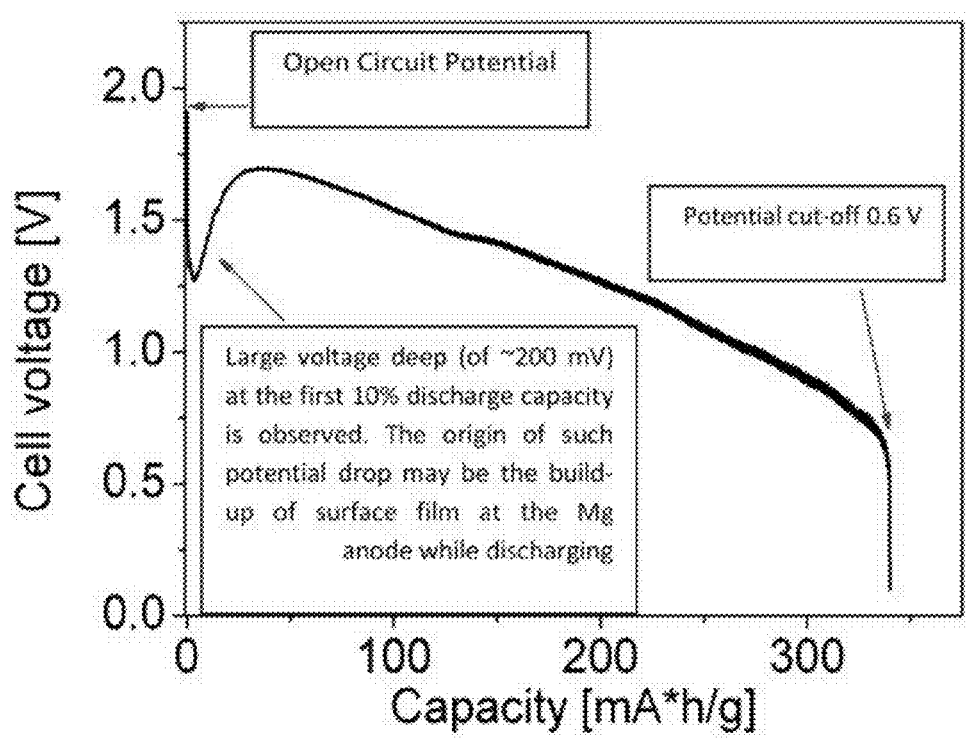

FIG. 19 presents a discharge curve of an Mg-air cell comprised of an Mg anode, a standard commercial air cathode and an electrolyte solution containing BMPTFSI+THF+EtBr at a volumetric ratio of 1:1:0.3 (0.1 mA/cm$^2$).

DESCRIPTION OF SPECIFIC EMBODIMENTS OF THE INVENTION

The present invention, in some embodiments thereof, relates to chemical synthesis and, more particularly, but not exclusively, to a novel process of preparing Grignard reagents and to uses thereof in organic syntheses.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present inventors have surprisingly uncovered that synthesis of a Grignard reagent can be performed electrochemically, when conducted in the presence of an electrolyte solution that comprises a room temperature ionic liquid (RTIL).

The present inventors have devised and successfully practiced an electrochemical process of preparing a Grignard Reagent (also abbreviated herein throughout as GR). The process has been demonstrated in an electrochemical cell constructed with a Mg working electrode into which a non-aqueous electrolyte solution containing an RTIL and a Grignard precursor (e.g., an alkyl halide or a compound of formula RX as defined herein) is introduced.

The preparation of various RMgX has been demonstrated using electrochemical methodologies and while further utilizing spectroscopic methods. Spectroscopic evidence of EtMgBr, as an exemplary GR, was gained through the use of $^1$H-NMR analyses. The linear dependence of product concentration on total charge passage has been established via potentiostatic experiments conducted at different time intervals, and a process mechanism has been suggested via the electrochemical corrosion hypothesis.

The electrochemical preparation of GR was demonstrated using an electrolyte solution which comprises, in addition to a RTIL, a non-aqueous polar solvent such as an ether. Low boiling and high boiling ethers were shown to be suitable solvents. Additionally, an Mg surface electropolishing phenomenon has been observed via SEM, AFM and visually, suggested as a process involving cation transport through a compact film composed of oxidized magnesium and reduced solvent species.

These processes and phenomena can be used with numerous different reagents and parameters in myriad applications for the benefit of pharmaceutical and chemical industries, and for research purposes. Exemplary applications include industrial bulk GR synthesis in a controlled flowing framework, electrolyte synthesis for magnesium batteries before and during discharge, and Mg electropolishing for surface finishing or smooth substrate preparation.

Embodiments of the present invention therefore relate to a fast, high-quantity, safe and controllable electrochemical processes of preparing a Grignard reagent, to electrochemical cells suitable for performing such processes and to processes and systems utilizing same in a flow scheme where the GR can be separated or reacted with a Grignard substrate in the same stream/stage and then separated, optionally while recycling the electrolyte solution or a part thereof.

Electrochemical Synthesis of Grignard Reagent:

According to an aspect of some embodiments of the present invention there is provided a process of preparing a Grignard reagent. The process, according to some embodiments of the present invention, comprises electrochemically reacting a Grignard precursor with an electrode that comprises a metal M suitable for forming a Grignard reagent, in the presence of an electrolyte solution that comprises a room temperature ionic liquid (RTIL).

As used herein, a Grignard reagent (also referred to herein throughout as GR) is an organometallic compound that is capable of effecting a Grignard-type reaction, as defined hereinafter.

In some embodiments, a Grignard reagent is a compound having a Formula RMX, wherein M is a metal suitable for forming a Grignard reagent, as defined herein; and X is halide, and R can be alkyl, alkenyl, alkynyl, cycloalkyl or aryl, substituted or unsubstituted, as these terms are defined herein, and can also be or comprises chemical groups such as, but not limited to, heteroaryl, heteroalicylic, alkoxy, aryloxy, thioalkoxy, thioaryloxy, carboxy, thiocarboxy, carbamate, thiocarbamate, amide, thioamide, carbonyl, thiocarbonyl, urea, and thiourea, as these terms are defined herein, each can be substituted or unsubstituted, as is further defined herein.

The halide X can be F, Cl, Br or I, and is preferably Cl, Br or I.

A Grignard precursor is an organic compound which is typically reacted with metal M to form the Grignard reagent. A Grignard precursor is typically a compound having a Formula RX, with R and X being as defined for a Grignard reagent.

A Grignard precursor can be, for example, an alkyl halide, an alkenyl halide, an alkynyl halide, a cycloalkyl halide or an aryl halide. Each of the alkyl, alkenyl, alkynyl, cycloalkyl and aryl can be substituted or unsubstituted as defined hereinbelow.

In some embodiments, the Grignard precursor is an alkyl halide such as, for example, ethyl bromide (bromoethane), ethyl chloride (chloroethane), ethyl iodide (iodoethane), propyl bromide (bromopropane), propyl chloride (chloropropane), propyl iodide (iodopropane), butyl bromide (bromobutane), butyl chloride (chlorobutane), butyl iodide (iodobutane), etc.

In some embodiments, the Grignard precursor is an aryl halide such as, for example, phenyl bromide, phenyl chloride and phenyl iodide.

Any other Grignard precursors and corresponding Grignard reagents, combining any of the definitions of R and X as presented herein are contemplated.

The metal M, suitable for forming a Grignard reagent is preferably magnesium (Mg), and can also be Lithium (Li) or any other metal that is suitable for forming a GR and participating in a Grignard-type reaction. Examples include ruthenium and several other transition metals.

It is expected that during the life of a patent maturing from this application many relevant Grignard reagent and corresponding Grignard precursors will be developed and the scope of the terms Grignard reagent and Grignard precursor is intended to include all such new technologies a priori.

An "electrode" as used herein and in the art is an electrically conductive element that may be connected to or form a part of an electric circuit.

An electrode as described herein can be shaped as a rod, a wire, a disc, a mesh, a powder and as any other acceptable shape, which should be recognized by those skilled in the art.

An electrode comprising metal M encompasses electrodes made of metal M in their entirety, electrodes made of a mixture which comprises metal M; electrodes coated with a material that comprises metal M or a material made of metal M, such that at least a portion of the electrode's surface comprises metal M or a mixture which comprises metal M.

When the electrode or the electrode's surface is made of a mixture that comprises the metal M, preferably the mixture comprises at least 50 weight percents of the metal M. In some embodiments, the mixture comprises at least 60, at least 70, at least 80, at least 90, at least 95, or at least 99 weight percents of metal M, including any intermediate value between 50 and 100 weight percents.

In some embodiments, the electrode consists essentially of metal M (e.g., being a pure metal M electrode such as, for example, a pure magnesium electrode).

By "pure" it is meant at least 95%, at least 96%, at least 97%, at least 98% or at least 99% metal M (e.g., Mg).

In some embodiments, the electrode is coated with metal M and the coating consists essentially of metal M.

When an electrode's coating comprises metal M, the electrode can be made of various materials, as is well-known in the art. The electrode can be coated with metal M-containing coating in its entirety or at least at a portion of the electrode that participates in the electrochemical reaction, namely, which contacts an electrolyte solution that comprises the reactant (herein, the Grignard precursor).

The electrode comprising metal M, in any of the configurations described herein, is also referred to herein as M-containing electrode and is exemplified as Mg-containing electrode.

In some embodiments, the Grignard precursor is present in the electrolyte solution, e.g., is dissolved within the electrolyte solution.

By "electrochemically reacting" the Grignard precursor and the M-containing electrode, it is meant that a reaction between the Grignard precursor within the electrolyte solution and the M-containing electrode is an electrochemical reaction, which involves electron transfer between the electrode and the electrolyte solution and/or the Grignard precursor within the electrolyte solution.

In some embodiments, the electrolyte solution comprising the Grignard precursor and the M-containing electrode form together a part of an electric circuit. Such an electric circuit further comprises an additional electrode which is electrically connected to the M-containing electrode, and which can also be in contact with the electrolyte solution.

Electrical connection is typically effected by means of electrical leads which connect the M-containing electrode to the additional electrode, either directly or indirectly (e.g., via a voltage source).

In some embodiments, the M-containing electrode is referred to herein as a working electrode in the electric circuit and the additional electrode is referred to as a counter or auxiliary electrode or can be a reference electrode.

By "working electrode" it is meant an electrode in an electric circuit that actively participates in an electrochemical reaction, namely, which reacts with the Grignard precursor, whereby a "counter electrode" is used to form the circuit, for gauging the potential of the working electrode and it functions by balancing the charge added or removed by the working electrode. In some embodiments, the electric circuit has a three-electrode configuration, as this term in widely recognized by any person skilled in the art, such that it further comprises a third, reference electrode. The reference electrode is a half cell with a known reduction potential and it acts as reference in measuring and controlling the working electrodes potential. The reference electrode does not pass any current, whereby the auxiliary (counter) electrode passes all the current needed to balance the current observed at the working electrode.

In some embodiments, the "electrochemically reacting" is performed in an electrochemical cell, which comprises a working electrode, a counter electrode and optionally a reference electrode, and which is configured for containing, or contains, an electrolyte solution which comprises the Grignard precursor, as described herein. In some embodiments of such an electrochemical cell, the working electrode and the counter electrode are electrically connected to one another, optionally by means of electric leads. In some embodiments of such an electrochemical cell, the M-containing electrode is the working electrode and typically functions as an anode, and an additional (counter) electrode typically functions as a cathode.

An exemplary electrochemical cell is described in further detail hereinafter.

In some of any of the embodiments described herein, electrochemically reacting the M-containing electrode and the Grignard precursor in the electrolyte solution comprises applying a voltage (potential) to the M-containing electrode.

The applied voltage is preferably selected in accordance with the electrochemical properties of the electrolyte solution, that is, within a range at which the electrolyte is not electrochemically reactive with the M-containing electrode.

In some embodiments, the applied voltage is measured as an applied potential of the working electrode (M-containing electrode) versus a reference electrode.

In some embodiments, the applied voltage is static, namely the same potential is applied throughout the electrochemical reaction, such that the electrochemical reaction is a potentiostatic process. Application of a static potential enables controlling the electrochemical processed in the cell by monitoring the generated current or current density. Alternatively, the applied voltage changes throughout the electrochemical reaction.

In some embodiments, the applied voltage ranges from about 0.01 Volt to about 10 Volts.

In some embodiments, the applied voltage is an applied potential that ranges from 0 Volt to 1 Volt, or from 0 Volt to 0.5 Volt versus a reference electrode such as a Mg reference electrode or a Pt reference electrode. In exemplary embodiments, it is 0.2 Volt versus a Mg reference electrode. In some embodiments, the voltage is applied during a time period that ranges from 1 minute to 60 minutes, depending, for example, on the concentration of the Grignard precursor, on the reaction volume, etc. For laboratory-scale processes, voltage application can be effected, for example, between 1 and 10 minutes.

In some embodiments, the applied voltage or potential and/or the application duration are such that generate a current density that ranges from about 0.5 mA/cm$^2$ to about 5 mA/cm$^2$, as defined herein, in an electrochemical cell that comprises the M-containing electrode and a counter electrode as described herein (and optionally a reference electrode).

In some embodiments, when voltage is applied during the process as described herein, an electrochemical cell in which such a process is effected further comprises a voltage source electrically connected to the electrodes.

In some of any of the embodiments described herein, electrochemically reacting the M-containing electrode and the Grignard precursor in the electrolyte solution comprises generating a current within an electrochemical cell in which the electrochemical reaction takes place. In some embodiments, a current is generated between the M-containing electrode and a counter electrode.

In some of these embodiments, generating a current is performed so as to provide a current density that ranges from about 0.5 mA/cm$^2$ to about 5 mA/cm$^2$, or from 1 mA/cm$^2$ to 3 mA/cm$^2$, including any intermediate value or subranges therebetween. Higher and lower values of current density are also contemplated.

In other embodiments, generating a current is performed so as to provide an electron charge [C] that passes through the electric circuit (through the electrochemical cell) that ranges from about 0.2 to about 2 [C], for an electrochemical cell of 300-600 microliters.

In some embodiments, generating a current is effected by applying a voltage, as described herein. In some embodiments, the voltage is applied so as to generate a current density and/or an electron charge through the circuit as defined herein.

The applied voltage is measured as a potential of the working electrode versus a reference electrode, and can be controlled so as to generate a current as described herein.

The measured current density and/or electron charge passes through the circuit is indicative of the electrochemical reaction as described herein, such that, for example, a decrease in the current and/or current density is indicative of reaction completion. Optionally, a drastic change in the current and/or current density is indicative of adverse electrochemical reactions in the cell.

Electrochemical Cell:

According to an aspect of some embodiments of the present invention there is provided an electrochemical cell configured for performing a process of preparing a Grignard reagent as described herein.

In some embodiments, the electrochemical cell comprises a working electrode and a counter electrode being electrically connected to one another. The working electrode in the electrochemical cell comprises a metal M, suitable for forming a Grignard reagent, as described herein, and is an M-containing electrode as described herein. The electrochemical cell is configured such that it is operable by introducing thereto a non-aqueous electrolyte solution and Grignard precursor as described herein.

Referring now to the drawings, FIG. 1B illustrates an exemplary electrochemical cell 30 for performing a preparation of a GR according to some embodiments of the present invention.

Exemplary electrochemical cell 30 is constructed for carrying out an electrochemical reaction for preparing Grignard reagent. Electrochemical cell 30 comprises element 34 for containing an electrolyte solution 36 as described herein and electrodes 18 and 20, optionally shaped as disc electrodes, configured such that at least a portion thereof is in contact with electrolyte solution 36. Electrodes 18 and 20 are each connected to an electrical lead 22, and can optionally be connected, via electrical leads 22 to a voltage source 28. Upon such connection, polarization of electrodes 18 and 20 is effected, and initiation or catalysis of the electrochemical reaction is performed.

The electrical current flowing in the thus closed electrical circuit can be measured and optionally monitored using a current measuring device (not shown). Other parameters, such as voltage, can also be measured, if desired, as known in the art (e.g., by measuring a potential versus a reference electrode).

FIG. 1A presents an exemplary electrochemical cell 40 for performing a preparation of a GR according to some embodiments of the present invention.

Exemplary electrochemical cell 40 is constructed for carrying out a potentiostatic process of electrochemically preparing a Grignard reagent. Electrochemical cell 40 comprises three cylindrical electrically-isolating and chemically inert (e.g., propylene) holders 42 fused together and serving as a scaffold. Element 34 configures for containing an electrolyte solution 36 as described herein in a form of a cylindrical cavity is enclosed within the scaffold, preferably at the center of middle holder 42. Electrodes 18 and 20, shaped as disc electrodes, are placed on either side of element 34. Electrodes 18 and 20 are each connected to an electrical lead 22 (e.g., a copper foil electrical terminal) and to other components in an electrical circuit, as described in FIG. 1B.

Middle holder 42 can have one or more (e.g., two) holes 54 allowing easy access to element 34, for example, for removing samples of electrolyte solution 36, or for introducing electrolyte solution 36 to element 34. One of holes 54 may serve for inserting a reference electrode to the cell.

The cell may optionally comprise element 56 serving for closing/opening cavity 34 and/or as support for the electrode 18. Electrochemical cell 40 can further comprise additional elements (e.g., voltage source) as described herein for electrochemical cell 30.

In some embodiments, electrodes 18 and 20 in electrochemical cell 40 or 30 in FIGS. 1A and 1B, respectively, are an anode and a cathode.

In some embodiments, the M-containing electrode as described herein, which is also referred to herein as the working electrode, functions as an anode in the electrochemical cell.

The counter electrode hence functions as a cathode in the electrochemical cell.

In some embodiments, the counter electrode can be any electrode suitable for use with a non-aqueous electrolyte solution as described herein. Exemplary counter electrodes comprise, for example, Mg-containing electrodes, Pt-containing electrodes, carbon electrodes (e.g., glassy carbon electrodes), silver electrodes and any other electrodes known in the art as usable as counter electrodes.

The electrochemical cell is operable by introducing thereto electrolyte solution 36, as described herein.

Electrolyte solution 36 as described herein preferably comprises a Grignard precursor as described herein.

In some of any of embodiments described herein, the electrochemical cell is operable by applying voltage (potential) thereto and/or by generating a current therein by means of, for example, a voltage source electrically connected to the counter electrode and the working electrode (the M-containing electrode), e.g., by means of electrical leads.

In some embodiments, an electrochemical cell as described in any one of the embodiments described herein comprises the non-aqueous electrolyte solution, as described herein, such that at least a portion of each of the working electrode and the counter electrode are in contact with the electrolyte solution. In such embodiments, the electrochemical cell is operable by introducing thereto a Grignard precursor as described herein (e.g., versus a hole such as hole 54 described in FIG. 1A). The electrochemical cell is further operable by connecting the electrodes to a voltage source.

In some embodiments, an electrochemical cell as described in any one of the embodiments described herein comprises the non-aqueous electrolyte solution and Grignard precursor, as described herein, optionally dissolved in the electrolyte solution, such that at least a portion of each of the working electrode and the counter electrode are in contact with the electrolyte solution and the Grignard reagent. In such embodiments, the electrochemical cell is operable by connecting the electrodes to a voltage source.

The Electrolyte Solution:

The term "electrolyte", as used herein, refers to a substance which can conduct electricity by charge displacement of charge carrier species.

Typically used electrolyte solutions consist of ions in solution and are typically known as ionic solutions comprising aqueous solutions of inorganic substances.

The present inventors have surprisingly uncovered that an electrochemical reaction process for preparing a Grignard reagent can be efficiently performed while utilizing an electrolyte solution which is essentially a non-aqueous electrolyte solution.

The phrase "non-aqueous electrolyte solution", as used herein, refers to a solution which comprises ionic conductors and which is devoid of water. By "devoid of" it is meant that the electrolyte solution comprises no more than 1, 0.5, 0.1, 0.05, 0.01 volume percent water, and can contain 0 percents water.

According to some embodiments of the present invention, the choice of non-aqueous electrolytes ranges from molecular liquids to room temperature ionic liquids (RTIL) to semi-solid solvents such as polymers. The ionic conductivity is dependent on several parameters related to both solvent (e.g. dielectric constant, viscosity, chemical composition) and also to certain extent on the salt (concentration, chemical composition).

According to some embodiments of the present invention, the non-aqueous electrolyte solution comprises a room temperature ionic liquid, also denoted herein throughout as its abbreviation RTIL.

The phrase "room temperature ionic liquid" or RTIL, as used herein, refers to a salt, typically of an organic substance, that have a sufficiently low melting point that allows it to be liquid at room temperature. In some embodiments, the term RTIL refers to salts that remain substantially liquid (do not solidify or boil) at a temperature range of −20–90° C.

By being a salt, an RTIL as described herein comprises a cation portion and an anion portion.

A cation of an RTIL typically comprises a bulky, optionally asymmetric, organic group.

Non-limiting examples of cations in RTIL include substituted or unsubstituted imidazolium cations, substituted or unsubstituted morpholinium cations, substituted or unsubstituted oxazolium cations, substituted or unsubstituted piperidinium cations, substituted or unsubstituted pyrazinium cations, substituted or unsubstituted pyrazolinium cations, substituted or unsubstituted pyrazolium cations, substituted or unsubstituted pyridazinium cations, substituted or unsubstituted pyridinium cations, substituted or unsubstituted pyrimidinium cations, substituted or unsubstituted pyrrolidinium cations, substituted or unsubstituted thiazolium cations, substituted or unsubstituted triazolium cations, substituted or unsubstituted 1,2,4-triazolinium cations, substituted or unsubstituted 1,2,3,4-tetrazolinium cations, tetraalkylammonium, alkylated phosphonium, allylated sulfonium, alkylated uronium and alkylated guanidinium.

By "alkylated" it is meant having 1, 2, 3 or more alkyl groups. Such alkyl groups can be replaced by alkenyls, alkynyls, aryl, cycloalkyls, each being substituted or unsubstituted.

Some non-limiting representative example of cations in an RTIL include 3-alkyl-1-methylimidazolium, 1-alkylpyridinium, N-methyl-N-alkylpyrrolidinium, 1-methyl-4-alkyl-1,2-triazolinium, 1-methyl-(2, 3 or 4)-alkyltetrazolinium, and N,N-diethyl-N-methyl-N-(2-methoxyethyl) ammonium.

In exemplary embodiments, a cation of a RTIL as described herein is a substituted or unsubstituted pyrrolidinium cation or a substituted or unsubstituted ammonium cation.

The aforementioned cations are coupled with one or more (e.g., 2, 3 or more, depending on the cation type) anions. The anion can be a simple halide or a charge delocalized larger group such as, for example, tetrafluoroborate, hexafluorophosphate, bistriflimide, triflate, tosylate, formate, alkylsulfate, alkylphosphate and glycolate.

Other suitable anions include, for example, perfluoro-1,1-dimethylpropyl alkoxides, mono- or di-perfluorosulfonate, $(CF_3)_2PF_4^-$, $(CF_3)_3PF_3^-$ $(CF_3)_4PF_2^-$, $(CF_3)_5PF^-$, $(CF_3)_6P^-$, $SF_5CF_2SO_3^-$, $SF_5CHFCF_2SO_3^-$, $(CF_3 SO_2)_2CH^-$, $(SF_5)_3C^-$, $(O(CF_3)_2C_2(CF_3)_2O)_2PO^-$ and $[F(FH)_n]^-$ onions wherein n=1-4). Alternatively, the anion is a non-Lewis acid-containing polyatomic anion having a Van der Waals volume exceeding 100 Å$^3$.

Representative, non-limiting example of anions include a halide, a triflate and bis(trifluoromethylsulfonyl)imide.

An RTIL, as described herein encompasses any combination of the cations and the anions as described herein. Any other RTIL is also contemplated.

It is expected that during the life of a patent maturing from this application many relevant RTILs will be developed and the scope of the term RTIL is intended to include all such new technologies a priori.

An exemplary RTIL demonstrated in the Examples section that follows is [1-butyl 1-methyl pyrolidinium bis(trifluoromethylsulfonyl)imide].

The non-aqueous electrolyte solution as described in any of the embodiments of the present invention can consist of a RTIL as the electrolyte, such that a concentration of the RTIL in the electrolyte solution, when taken together with Grignard precursor, is about 100 vol. percents.

In some embodiments, the electrolyte solution further comprises a non-aqueous solvent.

In some embodiments, the solvent is a polar non-aqueous solvent.

Exemplary polar organic liquids which are suitable to serve as solvents in non-aqueous electrolytes include, without limitation, linear ethers, cyclic ethers (e.g., dioxanes), esters, carbonates, lactones, nitriles, amides, sulfones, sulfolanes, diethylether, dimethoxyethane, tetrahydrofuran, dioxane, dioxolane, methyltetrahydrofuran, methyl formate, ethyl formate, methyl propionate, propylene carbonate, ethylene carbonate, dimethyl carbonate, diethyl carbonate, ethylmethyl carbonate, dibutyl carbonate, butyrolactones, acetonitrile, benzonitrile, nitromethane, nitrobenzene, dimethylformamide, N-methylpyrolidone, dimethylsulfone, tetramethylene sulfone, sulfolane and thiophene.

In some embodiments, the non-aqueous polar solvent is selected capable of stabilizing the obtained Grignard reagent, by being capable of coordinating the Mg atom in the reagent. Exemplary such solvents are those having an oxygen or sulfur atom bonded to an electron donating group such as alkyl. A representative example is an ether.

In some embodiments, the solvent comprises ether.

The ether can be a linear ether or a cyclic ether, and can further be divided into low boiling ethers (ethers exhibiting a low boiling point, for example, lower than 80° C., or lower than 70° C., such as, for example, diethyl ether and tetrahydrofuran THF) and high boiling ethers (ethers exhibiting a high boiling point, for example, higher than 80° C., or higher than 100° C. and even higher than 200° C.).

When a polar non-aqueous solvent is present in an electrolyte solution as described herein, a concentration of the RTIL is the electrolyte solution is at least 5 volume percents.

In some embodiments, a concentration of the RTIL is the electrolyte solution is at least 10 volume percents, at least 20, at least 30, at least 40 or at least 50 volume percents, including any intermediate value between 10 and 50 volume percents. Higher volume percentages of the RTIL in the electrolyte solution are also contemplated.

In some embodiments, a volumetric ratio between the RTIL and a non-aqueous polar solvent as described herein: ranges from 10:1 to 1:10, wherein any intermediate volumetric ratio is contemplated.

In some embodiments, the volumetric ratio of an RTIL and a polar non-aqueous solvent in the electrolyte solution is 10:1, 5:1, 2:1, 3:1, 1:1, 1:2, 1:3, 1:5 or 1:10.

In some embodiments, the volumetric ratio of an RTIL and a polar non-aqueous solvent ratio is 1:1.

A suitable RTIL, and an optional additional polar non-aqueous solvent are selected by the electrochemical properties thereof, and particularly as exhibiting an electrochemical window of at least 1 Volt, preferably at least 1.5 Volt, or at least 2 Volts.

By "electrochemical window" it is meant a voltage range at which the RTIL is non-reactive electrochemically, namely, does not produce an electric current upon application of a voltage within this range.

In any one of the embodiments of the present invention presented hereinthroughout, the Grignard precursor is mixed with (e.g., dissolved in) the electrolyte solution as described herein and forms a part of the electrolyte solution.

Hence, whenever "an electrolyte solution" is referred to, it is to be understood that in some embodiments, the electrolyte solution further comprises the Grignard precursor, as described herein.

A concentration of the Grignard precursor in the electrolyte solution can range, for example, from 1 to 50 volume percents, or from 1 to 20 volume percents, or from 5 to 20 volume percents, including any intermediate value and any intermediate subrange between 1 and 50 volume percents.

In some of any of the embodiments described herein, an electrolyte solution comprises a RTIL as described herein, a non-aqueous polar solvent (e.g., an ether) as described herein and the Grignard precursor. The RTIL and the polar solvent serve as the electrically conductive electrolyte, and the Grignard precursor participates in the electrochemical reaction.

In some of these embodiments, the ratio between the 3 components can vary as desired. In some of these embodiments, the ratio between the RTIL, the polar solvent and the Grignard precursor is such that a total concentration of the RTIL and the Grignard precursor in the electrolyte solution is at least 10 volume percents, and can range from 10 to 50 weight percents.

In exemplary embodiments, the volumetric ratio of the RTIL, the polar solvent and the Grignard precursor is 1:1:0.3, however, any other volumetric ratio is also contemplated.

The Grignard Reagent Product:

A product of an electrochemical process as described herein is a Grignard reagent as described herein, of Formula RMX, with R, M and X being as defined herein for M and RX.

In some embodiments, the process as described herein further comprises isolating the obtained Grignard reagent.

At the end of the electrochemical reaction, the obtained Grignard reagent is present in the electrolyte solution. Isolation of the Grignard reagent can be effected by means of, for example, removing the electrolyte solution from a reactor where the process was effected (e.g., an electrochemical cell as described herein), and isolating the Grignard reagent from the electrolyte solution. Methods for isolating the Grignard reagent from an electrolyte solution as described herein are known in the art and may include, for example, distillation.

Alternatively, the Grignard reagent is not isolated and the electrolyte solution containing the Grignard reagent is utilized as is in, for example, a Grignard-type reaction.

The presence and amount of a Grignard reagent in the electrolyte solution during the electrochemical reaction and once reaction is ceased or completed can be readily determined by analytical methods.

As demonstrated in the Examples section that follows, a reliable identification of a presence and/or amount of a Grignard reagent obtained by the described process can be performed by spectroscopic methods such as Nuclear Magnetic Resonance (NMR) and/or color reactions, during the process and once it is ceased or completed.

In some embodiments, monitoring a presence and/or amount of a Grignard reagent formed by the described process is effected by NMR, and, in some embodiments, by $^1$H-NMR.

By monitoring the reaction progress during the process, it can be determined when the electrochemical process can be ceased. Ceasing the process can be effected, for example, by discontinuing an application of voltage.

Applications:

A process as described herein can be utilized in a variety of applications.

In some of any of the embodiments described herein, a process as described herein is used in a synthesis of a compound whereby the synthesis comprises a Grignard-type reaction.

According to an aspect of some embodiments of the present invention there is provided a method of preparing a compound synthesizable by a synthesis that comprises a Grignard-type reaction.

The method, according to some embodiments of this aspect, comprises preparing a Grignard reagent by electrochemically reacting a Grignard precursor of a formula RX with an electrode which comprises metal M, in the presence of an electrolyte solution that comprises a room temperature ionic liquid, as described herein; and performing the Grignard-type reaction with the obtained Grignard Reagent.

The compound can be an organic compound or an organometallic compound.

The compound can be a final product of an organic synthesis which comprises in one or more steps of the synthesis a Grignard-type reaction, such that a method as described herein further includes other synthetic steps for preparing the compound.

Alternatively, the compound can be an intermediate in a synthesis of a final product.

A product of the Grignard-type reaction as described herein is also referred to herein as a Grignard product. The Grignard product can be a compound as described in these embodiments or an intermediate in the synthesis of such a compound, in which case the compound is also referred to herein as a "final product".

A "Grignard reagent" as used herein encompasses any compound, typically an electrophile, that can undergo a Grignard-type reaction as described herein in the presence of a Grignard reagent as described herein.

In some embodiments, the Grignard reagent is obtained by a process as described herein and is used in the Grignard-type reaction as is, namely, as an electrolyte solution as described herein, containing the Grignard reagent. Alternatively, the Grignard reagent is isolated from the electrolyte solution or from a part thereof.

In some embodiments, preparing the Grignard reagent and performing the Grignard-type reaction are effected within the same reactor, as exemplified, for example, in FIG. 18 and is further described in detail hereinafter.

In some embodiments, preparing the Grignard reagent and performing the Grignard-type reaction are effected is different reactors. The reactors, however, can be in fluid communication such that once a Grignard reagent is prepared, it is transferred, optionally flowed, to a reactor where a Grignard-type reaction is performed, where it is reacted with a Grignard reactant, as described herein, to afford a Grignard product, as described herein.

As used herein and is known in the art, a Grignard-type reaction is a reaction that utilizes a Grignard reagent, which is also referred to in the art as "Grignard reaction".

In most Grignard-type reactions, R in the RMX Grignard reagent functions as a nucleophile, and interacts with an electrophile. Most common Grignard-type reaction involve a C—C bond formation, formed between the nucleophilic R group of the Grignard reagent and an electrophilic carbon of a Grignard reactant, however, any other Grignard-type reactions are also contemplated.

Exemplary Grignard-type reactions include, but are not limited to, reactions with carbonyl-containing compounds, as exemplified in Scheme 2 below; reactions with other electrophiles, such as, for example, nitrile-containing compounds, disulfide-containing compounds, halide-containing compounds, imine-containing compounds, peroxide-containing compounds and heteroalicyclic compounds in which the heteroatom is an electron-withdrawing atom (e.g., oxygen), as exemplified in Scheme 3 below; reactions for forming a bond with a heteroatom such as, for example, P, Sn, B and Si, as exemplified in Scheme 4 below, reactions with transition metal halides in which one or more ligands are replaced by the R group of the Grignard reagent; reactions involving carbon-carbon coupling, for example, with a reactant such as aryl halide or alkyl halide; oxidations reactions, in which the Grignard reagent reacts with oxygen to produce peroxides or alcohols, as exemplified in Scheme 5 below. Any other Grignard-type reaction is also contemplated.

Scheme 2
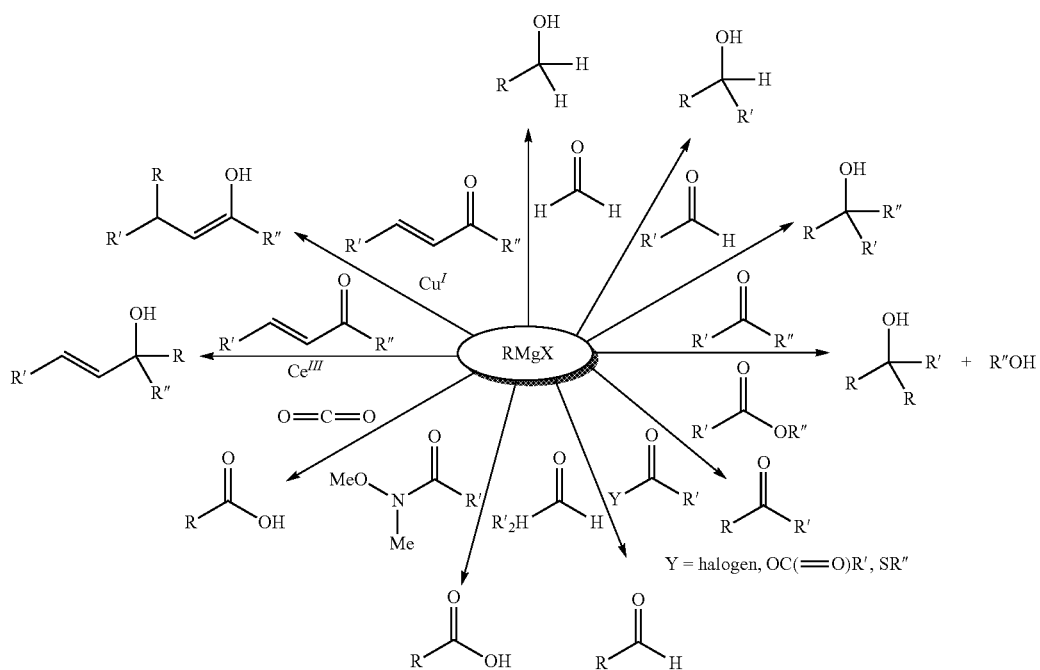
Scheme 3
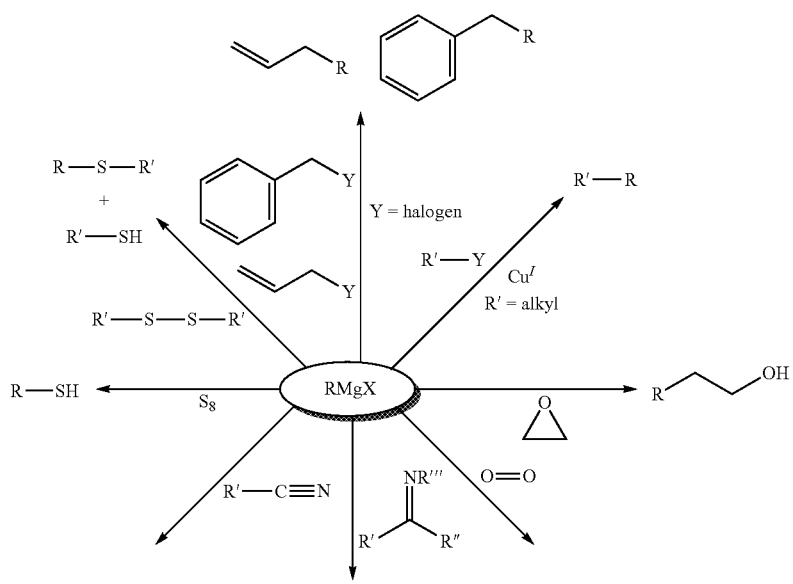
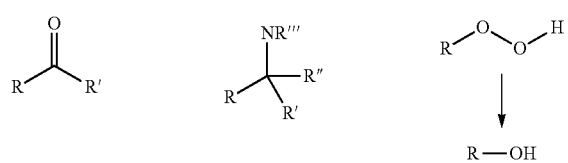

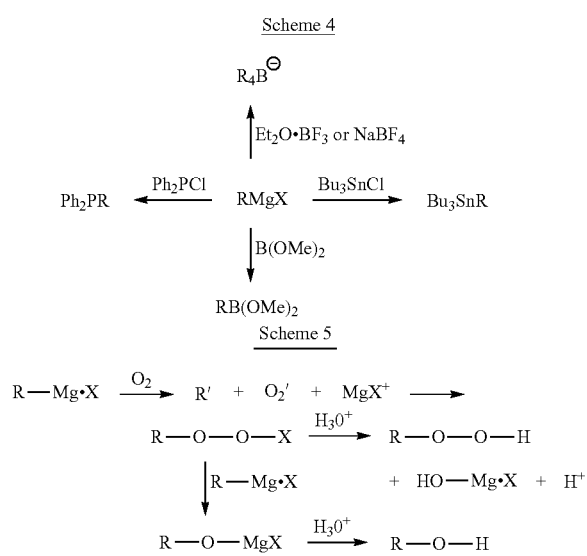

Scheme 4

Scheme 5

It is expected that during the life of a patent maturing from this application many relevant Grignard-type reactions, Grignard reagents and Grignard products will be developed and the scope of the terms Grignard-type reaction, Grignard reagent and Grignard product is intended to include all such new technologies a priori.

In some embodiments, the compound obtained by a method as described herein is a final product or an intermediate of a final product, whereby the final product can be, for example, a pharmaceutically active compound which is synthesized while performing a Grignard-type reaction as described herein in one or more steps of the synthesis. Representative example include tramadol, tamoxifen and naproxen. A synthesis of tramadol using a method as described herein is exemplified in FIG. 17.

The final product can be, for example, a reagent used in the polymer industries, such as an organo-tin compound, as depicted in Example 4 in the Examples section that follows.

Any other compounds obtainable by a method as described herein are contemplated herein.

According to an aspect of some embodiments of the present invention, there is provided a compound (e.g., an intermediate or a final product) obtained by a method as described herein. The product can be any compound synthesizable by a synthesis that comprises a Grignard-type reaction, namely, which is a product of a Grignard-type reaction as described herein, or a compound which utilizes a product of a Grignard-type reaction (a Grignard product) as an intermediate in its synthesis.

According to an aspect of some embodiments of the present invention, there is provided a system for preparing a compound synthesizable by a synthesis that comprises a Grignard-type reaction as described herein.

In some embodiments, the system comprises a reactor which comprises:

a working electrode and a counter electrode configured such that there is a liquid passage therebetween, the working electrode having a metal M, suitable for forming a Grignard reagent, as defined herein (being a M-containing electrode, a described herein);

a first inlet port for introducing into the reactor an electrolyte solution comprising a room temperature ionic liquid, as described herein, to generate a flow within the liquid passage; and a second inlet port for introducing into the reactor a Grignard precursor as described herein, the second inlet port being positioned upstream the liquid passage, such that a mixture of the Grignard precursor and the electrolyte solution is passed through the liquid passage between the working and counter electrodes.

In some embodiments, the reactor further comprises an outlet port, positioned downstream the liquid passage, for removing an electrolyte solution containing a Grignard reagent formed upon passing the liquid passage, from the reactor.

In some embodiments, the removed electrolyte solution containing a Grignard reagent is passed through a liquid passage to another reactor, for reacting with a Grignard reagent, as described herein, to thereby provide the a Grignard product as described herein, and optionally a final product as described herein.

In some embodiments, reacting with the Grignard reagent is performed within the reactor as described herein and the reactor further comprises a third inlet port for introducing into the reactor a Grignard reactant, namely, a reactant suitable for undergoing a Grignard-type reaction to thereby afford a Grignard product as described herein. The third inlet port is positioned downstream the liquid passage.

In these embodiments, the reactor may further comprise an outlet port positioned to remove a solution containing the formed Grignard product from the reactor.

In some embodiments, the system further comprises a recycling system configured for separating the formed Grignard reagent or Grignard product from a solution containing same, and to provide a solution containing the RTIL and for recycling the RTIL back into the first inlet port. Separating (isolating) the Grignard reagent or Grignard product from a reaction solution containing same can be performed by any method known in the art, including, for example distillation, filtration, chromatography, etc.

In some of any of the embodiments described herein, the electrolyte solution which generate the flow in the reactor and is introduced via the first inlet port, comprises RTIL as described herein, and further comprises a non-aqueous polar solvent as described herein.

In some embodiments, the electrolyte solution comprises RTIL without a polar solvent and is mixed with the polar solvent within the reactor, by means of, for example, another inlet port, positioned upstream the liquid passage.

In some embodiments, the reactor comprises an inert atmosphere (e.g., devoid of oxygen).

In some embodiments, the system further comprises means for generating a flow with the liquid passage and optionally within the reactor or the entire system (further comprising an additional reactor and/or a recycling system). Such means can include a pump, mixing devices and any other means for generating a flow of the electrolyte solution as described herein.

The volume of a reactor in any of the embodiments of a system as described herein can range from microliters to few dozen liters and even more.

In some embodiments, a process of preparing a GR as described herein can be utilized for preparing improved electrolyte solutions for use in a battery.

An exemplary such battery can be an electrochemical cell as described herein. In some embodiments, the counter electrode is configured as an air cathode such that the battery is a metal M-air battery, wherein metal M is as defined herein. An operation of an exemplary such cell is demonstrated in the Examples section that follows.

Any cathode configured as an air cathode can be used.

For example, an electrochemical cell as described herein can be constructed and operated in the presence of an electrolyte solution and a Grignard precursor as described herein. As a result, the electrolyte in such a cell comprises the formed Grignard reagent within a non-aqueous electrolyte solution that comprises an RTIL as described herein. This electrolyte and the M-containing electrode can then be utilized within a battery that comprises, for example, an air cathode, and the battery can be utilized as a discharging device, as is known in the art.

In another aspect of some embodiments of the present invention, a process as defined herein is utilized in a method of polishing a magnesium-containing surface of a substance. In some embodiments, such a method comprises electrochemically reacting, as described herein, a substance having a metal M-containing surface in the presence of an electrolyte solution that comprises RTIL, as described herein, wherein the surface of the substrate functions as an electrode as described herein. In some embodiments, the method is effected by utilizing the metal M-containing surface or substance as an electrode in an electrochemical cell for performing a process as described herein, by electrically connecting it to another electrode and applying a voltage.

In some embodiments, the metal M-containing surface or substance is used as an electrode to which a positive potential is applied (e.g., an anode in a case of potentiostatic operation).

In some embodiments, M is magnesium.

As used herein throughout, the term "alkyl" describes a saturated aliphatic hydrocarbon including straight chain and branched chain groups. Preferably, the alkyl group has 1 to 30 carbon atoms. Whenever a numerical range; e.g., "1-30", is stated herein, it means that the group, in this case the alkyl group, may contain 1 carbon atom, 2 carbon atoms, 3 carbon atoms, etc., up to and including 30 carbon atoms. In some embodiments the alkyl group has 1-20 carbon atoms. In some embodiments, the alkyl group has 1-10 carbon atoms. In some embodiments, the alkyl group has 1-4 carbon atoms. Exemplary alkyl groups include, but are not limited to methyl, ethyl, propyl, butyl, pentyl, hexyl, heptyl, octyl, nonyl, decyl, undecyl, dodecyl, tridecyl, tetradecyl, pentadecyl, heptadecyl, octadecyl and nonadecyl. The alkyl can be substituted or unsubstituted.

The term "alkenyl" describes an alkyl group, as defined herein, which consists of at least two carbon atoms and at least one carbon-carbon double bond.

The term "alkynyl" describes an alkyl group, as defined herein, which consists of at least two carbon atoms and at least one carbon-carbon triple bond.

The term "cycloalkyl" describes an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted.

The term "aryl" describes an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted.

When an alkyl, alkenyl, alkynyl, aryl, cycloalkyl, heteroalicyclic and heteroaryl is substituted, the substituent group can be, for example, alkyl, cycloalkyl, aryl, heteroaryl, heteroalicyclic, hydroxy, alkoxy, aryloxy, thiohydroxy, thioalkoxy, thioaryloxy, cyano, carbonyl, thiocarbonyl, O-carbamyl, N-carbamyl, O-thiocarbamyl, N-thiocarbamyl, C-amido, N-amido, C-carboxy, O-carboxy, nitro, sulfonamido, trihalomethanesulfonamido, silyl, guanyl, guanidino, ureido, amino or NRaRb, as defined herein, wherein Ra and Rb are each independently hydrogen, alkyl, cycloalkyl, aryl, carbonyl, sulfonyl, trihalomethysulfonyl and, when combined, a five- or six-member heteroalicyclic ring.

The term "alkoxy" describes both an —O-alkyl and an —O-cycloalkyl group, as defined herein.

The term "aryloxy" describes both an —O-aryl and an —O-heteroaryl group, as defined herein.

The term "thioalkoxy" describes both an —S-alkyl group, and an —S-cycloalkyl group, as defined herein.

The term "thioaryloxy" refers to both an —S-aryl and an —S-heteroaryl group, as defined herein.

The term "cyano" or "nitrile" describes a —C≡N group.

The term "carbonyl" describes a —C(=O)—R' group, where R' is hydrogen, alkyl, cycloalkyl, aryl, heteroaryl (bonded through a ring carbon) or heteroalicyclic (bonded through a ring carbon) as defined herein.

The term "ketone" describes a R'—C(=O)—R" group, where R' is as defined herein and R" is as defined for R', independently.

The term "thiocarbonyl" describes a —C(=S)—R' group, where R' is as defined herein.

The term "thioketone" describes a R'—C(=S)—R" group, where R' and R" are as defined herein.

The term "carbamate" describes an —OC(=O)—NR'R" group, where R' is as defined herein and R" is hydrogen, alkyl, cycloalkyl, aryl, heteroaryl (bonded through a ring carbon) or heteroalicyclic (bonded through a ring carbon) as defined herein, or a R'OC(=O)—NR"— group, where R' and R" are as defined herein.

The term "thiocarbamate" describes an —OC(=S)—NR'R" group, where R' and R" are as defined herein, and an R"OC(=S)NR'— group, where R' and R" are as defined herein.

The term "amide" describes a —C(C=O)—NR'R" group, where R' and R" are as defined herein, and an R'C(=O)—NR" group, where R' and R" are as defined herein.

The term "carboxy" describes a —C(=O)—O—R' groups, where R' is as defined herein, and an R'C(=O)—O— group, where R' is as defined herein.

The term "nitro" group describes an —NO$_2$ group.

The term "sulfonamide", encompasses both an "S-sulfonamido" and "N-sulfonamido" wherein an "S-sulfonamido" group describes a —S(=O)$_2$—NR'R" group, with R' is as defined herein and R" is as defined for R'. An "N-sulfonamido" group describes an R'S(=O)$_2$—NR" group, where R' and R" are as defined herein.

The term "trihalomethanesulfonamido" group refers to an $T_3CS(=O)_2NR'$— group, wherein T is a halo group as defined herein and R' is as defined herein.

The term "urea" group describes an —R'NC(=O)—NR"R'" group, where R', R" and R'" as defined herein.

The term "guanyl" group describes an R'R"NC(=N)— group, where R' and R" are as defined herein.

The term "silyl" describes a —SiR'R"R'", where R', R" and R'" are as defined herein.

The term "amino" group describes an —NR'R" group, where R' and R" are as described herein.

The term "sulfone" group describes an —S(=O)$_2$—R' group, where R' is as defined herein.

The term "sulfoxide" describes as S(O)R' group, with R' as defined herein.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof. Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the terms "method" and "process" are used herein interchangeably and refer to manners, means, techniques and procedures for accomplishing a given task including, but not limited to, those manners, means, techniques and procedures either known to, or readily developed from known manners, means, techniques and procedures by practitioners of the chemical art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Experimental Methods

Materials:

1-butyl-1-methyl pyrolidinium bis(trifluoromethylsulfonyl)imide (BMPTFSI) was purchased from IoLiTec corp. (>99%), dried under ultra high vacuum for 8 hours ($H_2O$<10 ppm) (its water content was measured with Karl Fischer (KF) titration using a 831 KF Coulometer (Metrohm)), and stored in an inert glove box (mbraun) with $H_2O$, $O_2$<1 ppm.

Bromoethane (EtBr; >99%), bromopropane (PrBr) and bromobenzene (PhBr) were purchased from Merck.

THF, Toluene, 2-butanol (>99.99%) and 2 2'-biquinoline were purchased from Sigma-Aldrich.

Organic solvents were dried with 3 Å-type (8-12 mesh) silica-alumina molecular sieves and stored in a glove box ($H_2O$<20 ppm, KF).

An electrolyte solution was prepared by mixing an RTIL (e.g., 1-butyl-1-methyl pyrolidinium bis(trifluoromethylsulfonyl)imide), a Grignard-reagent precursor (e.g., bromoethane) and an optional stabilizing agent such as an ether. Two exemplary of ethers were used: tetrahydrofuran (THF) and tetraethylene glycol dimethyl ether. An exemplary electrolyte solution was formed by mixing BMPTFSI, THF and EtBr at a volumetric ratio of 1:1:0.3, respectively, however, other volume ratios are contemplated, preferably such that at least the RTIL and the Grignard-reagent precursor constitute a volume percentage that ranges from 10% 50%.

Electrochemical Experiments:

Electrochemical experiments were performed using an EG&G potentiostat/galvanostat 2273 (Princeton Applied Research).

FIG. 1A presents a schematic illustration of an exemplary laboratory electrochemical cell 40 constructed for carrying out the potentiostatic process in which electrochemical GR synthesis is demonstrated and scrutinized. Three cylindrical propylene holders (42 in FIG. 1A) are fused together and serve as a scaffold, where an electrolyte solution (36 in FIG. 1A) is held in a cylindrical cavity (34 in FIG. 1A) at the center of the middle holder. Two holes 54 through the top of the middle holder 42 allow easy access to cavity 34. An electrolyte solution, with or without a Grignard precursor can be introduced into the cell through one of holes 54. One of holes 54 can be utilized for connecting the cell to a reference electrode (e.g., Mg reference electrode) (not shown). Two pure Mg and/or Pt electrodes (18 and 20 in FIG. 1A), each connected to a copper foil electrical terminal (22 in FIG. 1A), are inserted into the cell on either side of the cavity.

A magnesium reference electrode was used in all experiments as it is commonly used for non-aqueous electrochemistry involving organic solvents and RTILs.

All experiments were conducted under an inert atmosphere.

Cyclic voltammetry (CV) studies were conducted in an electrochemical cell as described herein (see, FIG. 1A) comprised of Pt and/or Mg as working, reference and counter electrodes, in various configurations (as detailed hereinbelow).

A galvanostatic or potentiostatic procedure was conducted on the cell where the potential on the working electrode was between 0-0.4 [V] Vs. the reference electrode. Scan rate employed was 5 mV/sec, unless otherwise indicated.

The following reaction occurred in the process:

RTIL(L)+ether(L)+RX(L)+Mg(S)(anode)→RTIL(L)+ ether(L)+RMgX(aq)

wherein R and X are as defined herein.

Analyses:

Scanning electron microscope (SEM, FEI Quanta 200), equipped with energy-dispersive X-ray spectroscopy system (EDS, Oxford Inst.) was utilized in surface morphology studies and chemical analysis. Before analyzing the Mg anode in the SEM, the electrodes were rinsed and cleaned with ethanol and dried under dry nitrogen flow.

$^1$H-NMR spectroscopy was conducted with a Bruker DPX 200 spectrometer, deuterium lock was established by inserting a separate Teflon capillary with deuterated methanol (MeOD) into NMR tubes. $^1$H-NMR was used to determine the molecular structure of the product species incorporating dissolved Mg ions and to indirectly calculate the product concentration.

AFM analysis was conducted with a XE-70 AFM analyzer (tapping mode, vertical resolution=1 nm Lateral resolution 15 nm). Tip: NT-MDT silicon NSG 30.

Example 1

Cyclic Voltammetry

The electrochemical windows of BMPTFSI and an electrolyte composed of BMPTFSI+THF in 1:1 volume ratio were determined by CV experiments using electrochemical cell as described hereinabove, having Pt working, reference and counter electrodes. The obtained data is presented in FIG. 2A and show that a particularly wide electrochemical window of about 5.5 [V] is observed for BMPTFSI. Such a wide electrochemical window is particularly required for processes which require dryness and use non-aqueous electrolytes, and indicates that the RTIL is advantageous as a stable electrolyte for the synthesis of GR, together with other general advantages such chemical and thermal stability, and low vapor pressure, as discussed hereinabove.

The presence of THF in the solution is intended for stabilizing the prepared Grignard reagent as well as for increasing electrolyte conductivity. It is observable from FIG. 2A that the addition of THF in 1:1 volume ratio to BMPTFSI narrows the solution's electrochemical window by about 1.9 [V].

In order to synthesize EtMgBr, a cell as described herein (see, FIG. 1A) was assembled. Two pure magnesium electrodes were polished in a glove box ($O_2$, $H_2O$<1 ppm) and inserted in a cell. A solution containing BMPTFSI+THF+EtBr at a volumetric ratio of 1:1:0.3, respectively, was introduced to the cell.

FIG. 2B presents the results of two cyclic voltamograms (CV's) conducted (anodic direction first); one with the working electrode being an Mg electrode, and the counter electrode being Pt electrode; and one with both working and counter electrodes being Mg electrodes. The cyclic voltamogram of a solution containing BMPTFSI+THF+EtBr at a volumetric ratio of 1:1:0.3, respectively, conducted with Pt working and counter electrodes is presented for comparison in FIG. 2B.

As shown in FIG. 2B, upon the activation of a CV no anodic or cathodic reaction overpotentials were observed; the anodic reaction occurred immediately with the application of potential and no evidence of any Mg passivation layer was observed despite the fact that the Mg anode was immersed in an organic medium. This is in contrast to the usually observed presence of a non-conductive passivating layer that inhibits the charge transport, even when the surface is only exposed to an inert atmosphere before immersion.

Without being bound by any particular theory, it is assumed that the interaction of the Mg surface with the RTIL electrolyte causes the passivation layer to disintegrate.

The obtained data indicate that there is an occurrence of chemically reversible dissolution and deposition of Mg in the electrolyte upon application of cyclic scanning. The deposition of Mg back onto the working electrode without electrolyte decomposition occurs only up to low overpotential of about 300 mV. The dissolution of Mg occurs without a parallel reaction involving electrolyte decomposition.

Evidently, when a platinum working electrode is replaced with a magnesium working electrode, high current densities are observable with negligible overpotential.

The corrosion current was calculated with an Evens diagram from a separate experiment (Tafel fit), with the same cell and electrolyte as described hereinabove.

The obtained data is presented in FIG. 3 and show that the observed corrosion current is about 20 μA/cm$^2$. It was also found that the corrosion rate does not change substantially after different time intervals, and after conducting additional CVs.

The CV as described hereinabove was tested also in processes of preparing other Grignard reagents. Examples include the following:

Bromomethane (MeBr)→methylmagnesium bromide (MeMgBr)

Bromopropane (MeBr)→propylmagnesium bromide (PrMgBr)

Bromobenzene (PhBr)→phenylmagnesium bromide (PhMgBr).

FIGS. 2C and 2D present the CV data obtained for processes of preparing PrMgBr (FIG. 2C) and for PhMgBr (FIG. 2D).

Example 2

Potentiostatic Process

The Potentiostatic Experiment:

Two pure magnesium electrodes were polished in a glove box ($O_2$, $H_2O$<1 ppm) and inserted in a cell containing an electrolyte as described in the materials and methods section hereinabove and illustrated in FIG. 1A.

In order to synthesize EtMgBr with a controlled concentration, a continuous constant potential of 0.2 [V] Vs. Mg reference electrode was applied to a cell utilizing Mg working and counter electrodes as described in Example 1 hereinabove, and using the electrolyte solution containing BMPTFSI+THF+EtBr, 1:1:0.3 vol %). The total charge passed through was calculated to be 0.805 [C].

The recorded potentiostatic (current transient) curve is presented in FIG. 4.

¹H-NMR Analyses:

¹H-NMR measurements were used in order to determine the molecular structure of the species, including the dissolved Mg, and to indirectly calculate the product concentration.

FIG. 5A presents ¹H-NMR spectrum of the pyrolidinium based cation (1-butyl 1-methyl pyrolidinium) in the ionic liquid BMPTFSI after drying, and FIG. 5B presents the spectrum of EtMgBr in THF (1.2 M). The molecular structures and signal ascription of the mentioned species are presented in FIG. 5C.

Once the location of the main signals has been established, an external reference solution was prepared by mixing BMPTFSI and THF/EtMgBr (EtMgBr dissolved in THF, 1.2 M) at a volumetric ratio of 1:1. FIG. 6 presents ¹H-NMR spectrum of the above solution. The structure and signal ascription of molecules from this graph are as presented in FIG. 5C.

As can clearly be seen, the spectral footprint of EtMgBr is observed at chemical shifts of about 0.53 ppm (triplet, J) and −1.39 ppm (quartet, K) when taking into consideration the signal identities of BMPTFSI, THF and EtMgBr from FIGS. 5A-C. The signal at −1.39 ppm (quartet, K) is most easily isolated and serves for determining presence and concentration of the GR.

FIG. 7A presents the ¹H-NMR spectrum of the electrolyte solution after a constant potential (potentiostatic) experiment as described hereinabove (in which the total charge transfer was 0.805 [C]). As can be seen therein, the spectrum includes the same peak shifts and H-coupling as seen with the reference solution sample in FIG. 6, and, notably, indicates a presence of EtMgBr in the solution after the potentiostatic experiment, as can be seen at shifts of 0.57 and (−1.33) ppm. An expansion of the 0.9-(−1.6) ppm range of the spectrum is presented in FIG. 7B, in which the signals which unequivocally belong to EtMgBr are marked. Exposition of this expansion and of an expansion of the spectrum depicted in FIG. 6 for the reference solution is presented in FIG. 7C, further confirming the formation of EtMgBr.

In FIG. 7C noticeable widening of peak-widths and a slight shift of about 0.05 ppm in peak positions relative to the spectrum in FIG. 6 is shown. This is probably due to the fact that both solutions were synthesized in two distinct ways, and while considering that the electrochemical formation of Grignard reagent is strongly exothermal.

FIG. 8 presents the ¹H-NMR spectrum of the electrolyte subsequent to the potentiostatic experiment. The signal of hydrogen atoms belonging to EtMgBr can be observed in the same manner as in FIG. 7B.

It is therefore demonstrated that higher boiling ethers are also usable in a process as described herein.

Example 3

Charge-Concentration Dependence

A relation between the charge transferred during the potentiostatic experiments and the final concentration of the obtained Grignard reagent was determined by applying a constant potential of 0.2 [V] Vs. Mg reference electrode at different time lengths to a number of cells, with each cell having a different value of total charge passing through it, as indicated in Table 1 below.

The different EtMgBr concentrations were calculated by taking the relative integration of the peak at (−1.39) ppm belonging to hydrogen on the "K" carbon in EtMgBr and the peak at 2.42 ppm belonging to hydrogen on the carbon "C" in the BMPTFSI cation (marked and presented in FIGS. 5A-C), as these two peaks are easily isolated.

In the RTIL reference solution seen in FIG. 6, it can be seen that the relative integration value is (2/8.51=0.235), and this value is calibrated to the known EtMgBr concentration in the same solution (0.6 M). As an example, for the ¹H-NMR results of the potentiostatic experiment presented in FIGS. 7A-B, the relative integration value is (2/26.58=0.0752); according to the calibration method described above, this indicates an EtMgBr concentration of 0.192 M in the final solution.

Table 1 below presents the data obtained in these studies.

The above concentration calculations were correlated with measurements conducted via volumetric titration of EtMgBr with 2-butanol. 1 M of 2-butanol in toluene was titrated into a tested electrolyte solution diluted with THF and containing the indicator 2,2 biquinoline, until a color change from red to yellow appeared, as depicted in FIG. 9. The amount of titrated 2-butanol was used to calculate the amount and concentration of EtMgBr in the electrolyte solution.

TABLE 1

| Cell | Calculated charge passed through cell [C] | integration of Hydrogen signal from "K" carbon on EtMgBr | integration of 3 Hydrogens on lone "C" methyl connected to nitrogen on BMPTFSI cation | Relative integration | estimated EtMgBr concentration [M] |
|---|---|---|---|---|---|
| Ref. solution: BMPTFSI + THF/1.2M EtMgBr at 1:1 Vol. | — | 2 | 8.51 | 0.235 | 0.6 |
| 1 | 0.420 | 2 | 56.09 | 0.036 | 0.091 |
| 2 | 0.805 | 2 | 26.58 | 0.075 | 0.192 |
| 3 | 1.06 | 2 | 25.64 | 0.078 | 0.199 |
| 4 | 1.338 | 2 | 21.32 | 0.094 | 0.239 |
| 5 | 1.451 | 2 | 18.65 | 0.107 | 0.274 |

Replacing THF by TEGDME:

Since THF is a relatively volatile ether (bp=66° C.), assays were performed also with higher boiling ether tetraethylene glycol dimethylether (TEGDME; bp=270° C.).

A potentiostatic experiment was performed as described hereinabove, using an electrolyte solution containing BMPTFSI+TEGDME+EtBr, at 1:1:0.3 volume ratio. The charge passed through the cell was 0.441 [C].

FIG. 10 presents a plot of the final GR concentration as a function of the charge passed through the cell (corresponding to the time of voltage application), and shows a linear correlation.

It is noted that the final concentrations are higher than should be if the reagents were to be synthesized as a result of electrochemical current alone with 300 μL of solution (also indicated by the positive intercept of the y axis), particularly when taking account of the corrosion current calculated when the cell is at rest.

In order to examine whether the GR synthesis is dependent on the application of potential, a cell identical to previous cells was assembled and filled with a THF-containing electrolyte as described hereinabove. The cell was left to rest, with no potential application, for 1500 seconds.

FIG. 11 presents the $^1$H-NMR spectrum of the obtained electrolyte solution, and clearly shows that the signals indicative of the presence of EtMgBr at 0.53 ppm (triplet, J) and −1.39 ppm (quartet, K) are missing.

These results indicate that without the application of a potential, the reaction occurs at a rate negligible enough so that the reaction products are undetectable, even when the calculated corrosion is considered.

Example 4

Mechanistic Insights

Without being bound by any particular theory, it suggested that the reaction involved in the process as described herein follows an electrochemical corrosion hypothesis which involves Mg oxidation and alkyl halide reduction [see, Richey, H. Grignard reagents—new developments; John Wiley and sons, LTD: New York, 2000].

The suggested mechanism is illustrated in FIG. 12. Mg is oxidized and dissolved into the electrolyte where it is coordinated with halide anions (products of alkyl halide reduction) or TFSI anions from the electrolyte. Following Mg oxidation, Mg ion species react with reduced alkyl species to form the GR.

The suggested mechanism is in line with the essential role demonstrated herein for the ionic conductivity of the electrolyte; with the positive potential on the Mg anode; and with the catalytic effect of applied potential.

Example 5

Magnesium Electropolishing Phenomenon

The effect of the process on the Mg electrode was tested. A cell as described hereinabove, and as used in Example 1, with a THF-containing electrolyte as described herein, was subjected to CV at a scan rate of 50 mV/sec (anodic direction first).

The obtained data is presented in FIG. 13. High current densities were observed together with typical anodic and cathodic reactions.

After the CV, the Mg counter electrode was extracted from the cell, cleaned with an alcohol and subjected to SEM. FIGS. 14A-B present SEM images of secondary electrons (SE), which provide a strong geometrical contrast. In FIG. 14A, a surface of an Mg electrode grinded using P180 grinding paper, 78 μm grit, before application of CV is shown. A Mg surface with clear roughness geometrical features is seen. In FIG. 14B, the electrode's surface after CV application is shown, and almost no contrast is observed, indicating a formation of an almost uniform smooth surface unlike the roughly grinded Mg surface before the experiment.

In order to gain more surface data, AFM analysis was conducted on the surface of the same Mg electrode subjected to CV. The surface morphology is presented in FIG. 15, and shows an average roughness (Ra) of 22 nm, and a root mean square roughness (Rq) of 27 nm.

The Mg surface after the CV can be seen visually in FIGS. 16A-B.

Without being bound by any particular theory, it is suggested that this phenomenon is caused by the presence of a thin compact solid film which allows the transfer of cations while suppressing crystallographic etching on the surface.

Example 6

Exemplary Applications

The electrochemical GR synthesis described herein can be varied and controlled using various RTILs and Grignard precursors, according to the desired system properties.

The process can be utilized in industrial chemical processes, using, for example, a flow reactor, followed by an optional reaction of the prepared Grignard reagent with a controlled feeding of electrophilic or other Grignard reactants along the flow for performing a Grignard-type reaction and affording a final synthetic product. Using such an overall synthetic process, Grignard reagent and Grignard products are synthesized in bulk while maintaining safety and controlled cost-effective mass production.

For example, industrial manufacturing of tramadol, a powerful analgesic synthesis, utilizing a process as described herein is presented in FIG. 17.

An additional example is synthesis of organo-tin compounds, which are widely used as stabilizers for vinyl chloride resins, as catalysts for hardening urethane, as catalysts for hardening silicon resin, and in other industrial applications. Thus, SnCl$_4$ can be converted to SnR$_4$ (with 4 equivalents of GR) using the process as described herein, a depicted in Scheme 6 below.

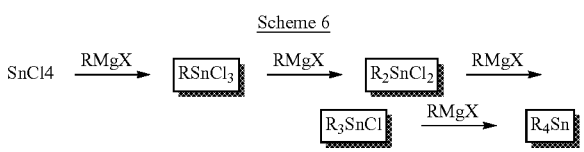

Scheme 6

An exemplary reactor utilizing a production of GR as described herein for industrial processes is schematically illustrated in FIG. 18. The reactor is comprised of a housing 1, a Grignard reactant inlet port 2, a Grignard precursor (e.g., an organic halide) inlet port 3, an electrolyte inlet port 4, and at least two metal electrodes (e.g., Mg electrodes) 9 and 10 having a liquid passage therebetween. RTIL-containing solution enters the reactor from recycled ionic liquid (IL) unit 6 via inlet port 4 during the course of operation. On arrival, the RTIL is mixed with a Grignard precursor (e.g., an organic halide) 12 and optionally with an additional solvent 11 (e.g., ether) and flow moves further along the flow path towards the anode and cathode (e.g., Mg-containing electrodes) 9 and 10. The electrodes are connected to a voltage supply (marked by circles) and are polarized so that electrode 10 undergoes dissolution while electrode 9 undergoes plating, thus securing the continuous presence of a fresh, bare Mg surface.

Organic halide 12 reacts with the Mg on a surface of electrode 9, forming GR 13. GR 13 along with RTIL-containing electrolyte flow moves further along the flow path towards Grignard reactant inlet port 2. On mixing with a Grignard reactant stream 14, a Grignard-type reaction takes place and the obtained Grignard product 15 leaves housing 1 through a Grignard product outlet port 5 along with the electrolyte solution stream. Product 15 is separated from the electrolyte solution in a separator system 7 and the recycled electrolyte solution stream moves to unit 6 and again toward the recycled inlet port 4, whereas the product is moved to a storage vessel through a product outlet 8.

The flow path can be driven to effect liquid passage through the reactor by means of, for example, a pump or mixing devices, as are known in the art.

A process as described herein can also be used in metal-air batteries, particularly for GR synthesis in electrolytes for magnesium batteries. Many magnesium batteries in research have electrolytes that include GRs or other organo-magnesium species. The synthesis of GRs directly from the Mg anode into the electrolyte creates desirably active magnesium species, and can be used as the anodic reaction in the battery itself.

For example, a magnesium-air cell equipped with a magnesium anode, an RTIL electrolyte as described herein and an air cathode (e.g., carbon-based air cathode) for supporting ambient oxygen reduction was constructed. A discharge curve from such a cell is presented in FIG. 19.

In addition, the phenomenon of Mg electropolishing in non-aqueous media, as demonstrated herein, can be utilized in industry and research for, for example, Mg finishing for various products, preparation of smooth Mg surfaces as substrates and other uses.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A process of preparing a Grignard Reagent of a formula RMX, the process comprising:
   electrochemically reacting an electrode comprising the M metal with a Grignard precursor having a formula RX in the presence of a non-aqueous electrolyte solution comprising a room temperature ionic liquid (RTIL),
   wherein:
   R is selected from the group consisting of alkyl, alkenyl, alkynyl, cycloalkyl, aryl, heteroaryl, heteroalicyclic, alkoxy, aryloxy, thioalkoxy, thioaryloxy, carboxy, thiocarboxy, carbamate, thiocarbamate, amide, thioamide, carbonyl, thiocarbonyl, urea, and thiourea;
   M is a metal suitable for forming a Grignard reagent; and
   X is halide,
   thereby preparing the Grignard Reagent.

2. The process of claim 1, wherein said metal M is selected from the group consisting of magnesium and lithium.

3. The process of claim 1, wherein said room temperature ionic liquid comprises a cation selected from the group consisting of a substituted or unsubstituted imidazolium, a substituted or unsubstituted morpholinium, a substituted or unsubstituted oxazolium, a substituted or unsubstituted piperidinium, a substituted or unsubstituted pyrazinium, a substituted or unsubstituted pyrazolinium, a substituted or unsubstituted pyrazolium, a substituted or unsubstituted pyridazinium, a substituted or unsubstituted pyridinium, a substituted or unsubstituted pyrimidinium, a substituted or unsubstituted pyrrolidinium, a substituted or unsubstituted thiazolium, a substituted or unsubstituted triazolium, a substituted or unsubstituted 1,2,4-triazolinium, a substituted or unsubstituted 1,2,3,4-tetrazolinium, phosphonium, sulfonium, uronium, guanidinium, 3-alkyl-1-methylimidazolium, 1-alkylpyridinium, N-methyl-N-alkylpyrrolidinium, 1-methyl-4-alkyl-1,2-triazolinium, 1-methyl-(2, 3 or 4)-alkyltetrazolinium and tetraalkylammonium.

4. The process of claim 3, wherein an anion of said room temperature ionic liquid is selected from the group consisting of a halide, a triflate and bis(trifluoromethylsulfonyl)imide.

5. The process of claim 1, wherein said room temperature ionic liquid is [1-butyl 1-methyl pyrolidinium bis(trifluoromethylsulfonyl)imide].

6. The process of claim 1, wherein said non-aqueous solution further comprises a polar non-aqueous solvent.

7. The process of claim 6, wherein said solvent comprises ether.

8. The process of claim 7, wherein said ether is selected from the group consisting of diethyl ether, THF and an ether having a boiling point higher than 80° C.

9. The process of claim 6, wherein a concentration of said room temperature ionic liquid is said non-aqueous solution is at least 5 volume percents.

10. The process of claim 1, wherein said electrolyte solution comprises said room temperature ionic liquid and a non-aqueous polar solvent at a volumetric ratio that ranges from 10:1 to 1:10.

11. The process of claim 10, wherein said ratio is 1:1.

12. The process of claim 1, wherein a concentration of said Grignard precursor in said electrolyte solution ranges from 1 to 50 volume percents.

13. The process of claim 1, wherein a sum of a concentration of said Grignard precursor and a concentration of said room temperature ionic liquid is at least 10 volume percents of said electrolyte solution.

14. The process of claim 12, wherein said electrochemically reacting comprises electrically connecting said electrode comprising said M metal with a counter electrode, wherein each of said electrode comprising said M metal and said counter electrode contacts said electrolyte solution.

15. The process of claim 14, wherein said electrochemically reacting further comprises generating an electric current between said electrodes.

16. The process of claim 15, wherein generating said electric current comprises generating a current density that ranges from 1 to 5 $mA/cm^2$.

17. The process of claim 14, wherein said electrode containing said M metal functions as an anode during said electrochemically reacting.

18. The process of claim 1, wherein the Grignard reagent and/or an amount of the Grignard reagent obtained by the process is identifyable by an analytical method selected from the group consisting of a color reaction and NMR.

19. The process of claim 1, further comprising isolating the Grignard reagent.

* * * * *